US012810046B2

United States Patent
(12) United States Patent
Horbatiuk et al.

(10) Patent No.: US 12,810,046 B2
(45) Date of Patent: Nov. 24, 2026

(54) SYSTEMS AND METHODS FOR MODELING FLUID FLOW

(71) Applicant: Wayne State University, Detroit, MI (US)

(72) Inventors: Jeffrey Horbatiuk, Shelby Township, MI (US); Carolyn Harris, Grosspointe Farms, MI (US); Lubna Alazzawi, Deer Point Heights, MI (US); Ahmad Faryami, Farmington Hills, MI (US)

(73) Assignee: Wayne State University, Detroit, MI (US)

( * ) Notice: Subject to any disclaimer, the term of this patent is extended or adjusted under 35 U.S.C. 154(b) by 954 days.

(21) Appl. No.: 18/005,583

(22) PCT Filed: Jul. 16, 2021

(86) PCT No.: PCT/US2021/042009
§ 371 (c)(1),
(2) Date: Jan. 13, 2023

(87) PCT Pub. No.: WO2022/016072
PCT Pub. Date: Jan. 20, 2022

(65) Prior Publication Data

US 2023/0274055 A1 Aug. 31, 2023

Related U.S. Application Data

(60) Provisional application No. 63/053,544, filed on Jul. 17, 2020.

(51) Int. Cl.
*G06F 30/28* (2020.01)
*A61F 2/24* (2006.01)
*G09B 23/30* (2006.01)

(52) U.S. Cl.
CPC ................ *G06F 30/28* (2020.01); *A61F 2/24* (2013.01); *G09B 23/303* (2013.01)

(58) Field of Classification Search
CPC .......... G06F 30/28; A61F 2/24; G09B 23/303
See application file for complete search history.

(56) References Cited

U.S. PATENT DOCUMENTS 4,682,491 A 7/1987 Pickard
7,348,175 B2 3/2008 Vilendrer et al.
(Continued)

FOREIGN PATENT DOCUMENTS

WO WO2010040699 A1 4/2010

OTHER PUBLICATIONS

Ahmed, et al., "New generation of bioreactors that advance extracellular matrix modelling and tissue engineering," Biotechnology Letters, vol. 41, 2019, pp. 1-25.
(Continued)

*Primary Examiner* — Jamel E Williams
(74) *Attorney, Agent, or Firm* — Lee & Hayes, P.C.

(57) ABSTRACT

Described herein are systems and methods for modeling fluid flow. The systems may comprise a plurality of chambers, a plurality of sensors, a pump, a plurality of valves, and a flow limiting operator (FLO). The respective sensor of the plurality of sensors may be configured to sense a respective monitoring parameter associated with the respective chamber. The pump may be configured to move media to or from the respective chamber. The respective valve of the plurality of valves may be configured to control a fluid velocity of the media flowing through the respective chamber. The FLO may be electrically connected to the plurality of sensors, the pump, and the plurality of valves. The FLO may be configured to independently control the respective chamber by manipulating one or more controllable parameters associated with the respective chamber based on the respective monitoring parameter associated with the respective chamber.

18 Claims, 18 Drawing Sheets

(56) References Cited

U.S. PATENT DOCUMENTS

| | | | | |
|---|---|---|---|---|
| 7,410,792 | B2 | 8/2008 | Vilendrer | |
| 8,173,420 | B2 | 5/2012 | Moreno et al. | |
| 8,852,923 | B2 | 10/2014 | Boronyak et al. | |
| 9,783,768 | B2 | 10/2017 | Larcher et al. | |
| 9,965,591 | B2 | 5/2018 | Christiansen et al. | |
| 2012/0060622 | A1 | 3/2012 | Harris et al. | |
| 2012/0122208 | A1 | 5/2012 | Fisher et al. | |
| 2014/0242681 | A1* | 8/2014 | Fiorentino ............. | C12M 23/06 435/292.1 |
| 2016/0083690 | A1 | 3/2016 | Birch et al. | |
| 2017/0101618 | A1 | 4/2017 | Kamen et al. | |
| 2017/0199507 | A1 | 7/2017 | Murphy et al. | |
| 2017/0349874 | A1 | 12/2017 | Jaques et al. | |

OTHER PUBLICATIONS

Benninghaus, et al., “Enhanced in vitro model of the CSF dynamics,” Fluids and Barriers of the CNS, vol. 16, No. 11, 2019, 11 pages.

Burova, et al., “Mathematical and computational models for bone tissue engineering in bioreactor systems,” J. Tissue Eng., vol. 10, 2019, pp. 1-25.

D’Costa, et al., “Biomaterials and Culture Systems for Development of Organoid and Organ-on-a-Chip Models,” Biomaterials—Engineering Cell Behavior, Ann. Biomed. Eng., vol. 48, 2020, pp. 2002-2027.

Hanak, et al. “Toward a better understanding of the cellular basis for cerebrospinal fluid shunt obstruction: report on the construction of a bank of explanted hydrocephalus devices,” J Neurosurg Pediatr., 18(2), Author manuscript, Aug. 2016, pp. 213-223.

Harris, et al., “Fabrication of three-dimensional hydrogel scaffolds for modeling shunt failure by tissue obstruction in hydrocephalus” Fluids and Barriers of the CNS, 12:26, 2015, pp. 1-15.

Harris, et al., “Mechanical contributions to astrocyte adhesion using a novel in vitro model of catheter obstruction,” Elsevier, Experimental Neurology 222, 2010, pp. 204-210.

Mundargi, et al., “Novel Sensor-Enabled Ex Vivo Bioreactor: A New Approach towards Physiological Parameters and Porcine Artery Viability,” BioMed Research International, vol. 2015, 2015, 8 pages.

Schurlein, et al., “A versatile modular bioreactor platform for Tissue Engineering,” Biotechnol. J., vol. 12, No. 2, 2017, pp. 1-11.

Zohar, et al., “Multi-flow channel bioreactor enables real-time monitoring of cellular dynamics in 3D engineered tissue,” Communications Biology, vol. 2, No. 158, 2019, 10 pages.

* cited by examiner

SYSTEMS AND METHODS FOR MODELING FLUID FLOW

STATEMENT REGARDING FEDERALLY SPONSORED RESEARCH OR DEVELOPMENT

This invention was made with government support under contract NS094570-0351 awarded by the National Institutes of Health. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

This disclosure relates to systems and methods for modeling fluid flow, including in the context of simulating flow of biological fluids in organs or tissues, such as cerebrospinal fluid in brain tissue, and blood in the circulatory system; as well as in production bioreactors. It relates further to systems and methods for testing the performance of medical implants and compounds during simulated circulation of fluids.

BACKGROUND OF ASPECTS OF THE DISCLOSURE

Currently, biomaterials go through a series of tests including computer simulations, well plate tests, constant pressure/flow rate in vitro tests, animal models, and human trials—many of which are focused on biocompatibility but not the efficacy of testing. However, there can be discrepancies between the in vitro, in vivo, in silico, and human models leading to millions more in research and development. A large part of this discrepancy can be attributed to the differences in physiologic environments between bioreactors, animals, and humans. Improvements aim to attenuate the discrepancies by creating a more efficient system for modeling fluid flow.

For example, hydrocephalus, an imbalance between cerebrospinal fluid (CSF) production and absorption, is diagnosed in more than 1 in 500 people in the United States. Approximately 80% of these patients will suffer long-term neurological deficits. Genetic diseases, meningitis, subarachnoid hemorrhage, stroke, traumatic brain injury, or tumors cause hydrocephalus.

The common treatment for all hydrocephalus patients is CSF drainage by shunting. Despite all efforts to date, shunts still have the highest failure rate of any neurological device. A shocking 98% of shunts fail after just ten years, a rate bumped up by the 80% of patients who suffer from tens if not hundreds of repetitive shunt failures. Shunts fail after becoming obstructed with attaching glia, creating a substrate for more glia or other cells and tissues (e.g. choroid plexus) to secondarily bind and block the flow of CSF through the shunt. For additional discussion, see US Patent Publication No. 2012/0060622 (Harris et al.).

Since glial attachment is believed to be a mechanism for shunt failure, it is important to discover what it is about the pathophysiology of hydrocephalus that causes glia to attach and cause repetitive shunt failure. Until these cues are identified, shunt failure cannot be addressed in a principled way.

Bioreactors have become an integral part of testing biomaterials and pharmaceuticals. Bioreactors are among the first steps for testing because they are faster, cheaper, and more controlled than most multi-factorial animal models. Bioreactors also act as an important intermediary between computer models and complex biological systems because mechanisms can occur freely instead of relying upon predicted simulations. Bioreactors need to be designed as physiologic as possible to test specific hypotheses. Many factors go into predicting a cell's behavior, including pressure, flow rate, and pulsation amplitude. However, to be an accurate model, these factors need to change over time, something with which current models struggle.

Systems and methods for modeling fluid flow may be improved in various aspects.

SUMMARY OF THE DISCLOSURE

Described herein are systems and methods for modeling fluid flow, controlling and monitoring volumetric flow rate, pressure, and flow amplitude of the desired fluid. In exemplary aspects, the desired fluid simulates a physiologic fluid, such as cerebrospinal fluid. In one aspect, an in vitro pulsatile flow system is used to control the flow of the desired fluid. In exemplary applications, the in vitro pulsatile flow system is used to monitor the adhesion of at least one component of the desired fluid to test material, such as a medical implant. The in vitro pulsatile flow system has a fluid reservoir that contains the desired fluid. The test material of the system is positioned in fluid communication with the desired fluid such that the desired fluid contacts at least a portion of the test material. In an additional aspect, the flow system includes a pump positioned between and in fluid communication with the fluid reservoir and the test material. In some aspects, when the test material is a medical implant having a bore, the pump is placed in direct fluid communication with the bore of the medical implant. In other aspects, the test material is placed within a housing that is placed in fluid communication with the pump. In a further aspect, the flow system has a pressure valve positioned between and in fluid communication with the test material and the fluid reservoir. Methods of using the bioreactor system, enhanced with FLO, to screen compounds and test materials for inhibition of cell adhesion are also disclosed.

Specifically provided herein are improvements (embodiments of which are referred to as Flow Limiting Operators; FLO) that allow control of the volumetric flow rate and pressure inside a fluid chamber, through fluid resistance instead of manipulating head gases. This improvement is closer to the body's control of pressure and allows for single stage compliance.

Also provided are systems that employ a single stage compliance chamber. Current technology uses a secondary chamber fluid and an air pocket to create secondary peaks like pulsations in the body. Embodiments of the FLO system integrate a single stage chamber to create the same waveforms using elastic materials and no air pockets.

The improvements described herein provide a device and system that can be used to fabricate any specific waveform functions over time, for instance in order to match the mean results of the population or a specific patient.

Also provided are embodiments that integrate flexible/detachable 360-degree imageable (e.g., transparent) chambers, for instance by using a substantially transparent component (such as vinyl) base for the chamber. In implementations, samples/media to be imaged may be fixed and then stained. Conventionally, the chamber may be imaged in situ. With the improvements, the flexible/detachable 360-degree imageable chamber together with the sample/media inside may be detached from other parts of the system and imaged. Moreover, the flexible/detachable 360-degree imageable chamber may be restored into the system after being imaged. By using the flexible/detachable 360-degree imageable chamber, the chamber is still intact and in a sterile environment for experiments to continue after being imaged. Moreover, because of the vinyl base, the single stage compliance chamber may be provided.

The improvements described herein create a long-term system in which the electronics and 3D scaffold can run for an extended period, such as more than seven days, at least two weeks, at least three weeks, at least four weeks, more than four weeks, at least a month, more than a month, or more than two months. Also provided are multiplexing improvements that provide high-throughput systems, for instance, capable of running multiple (for example, more than 4, more than 8, etc.) chambers in parallel. Optionally, condition(s) in two or more of the parallel chambers can be independently controlled.

Thus, various embodiments provided higher throughput, less mechanical complexity regarding waveform generation, longer chronic data runs, better representation of surrounding tissue scaffolds, and easier imaging during experiments.

An aspect of this disclosure provides a system for modeling fluid flow. The system may comprise a plurality of chambers, a plurality of sensors, one or more pumps, a plurality of valves, and a flow limiting operator (FLO). A respective chamber of the plurality of chambers may have a respective primary end and a respective secondary end. A respective sensor of the plurality of sensors may be connected to the respective primary end or the secondary end of the respective chamber. The respective sensor may be configured to sense a respective monitoring parameter associated with the respective chamber. The one or more pumps may be connected to the respective primary end of the respective chamber. The one or more pumps may be configured to move media to or from the respective chamber. A respective valve of the plurality of valves may be connected to the respective secondary end or the primary end of the respective chamber. The respective valve may be configured to control a fluid velocity of the media flowing through the respective chamber. The FLO may be electrically connected to the plurality of sensors, the pump, and the plurality of valves. The FLO may be configured to independently control the respective chamber by manipulating one or more controllable parameters associated with the respective chamber based on the respective monitoring parameter associated with the respective chamber.

In some instances, the system may further comprise a reservoir, connected between the pump and the respective valve. The reservoir may be configured to contain the media.

In some instances, the system may further comprise a plurality of additional sensors. A respective additional sensor of the plurality of additional sensors may be connected to the respective secondary end or the primary end of the respective chamber. The respective additional sensor may be configured to sense a respective additional parameter associated with the respective chamber.

In some instances, the FLO may be further configured to be electrically connected to the plurality of additional sensors. The FLO may be configured to receive the respective additional parameter associated with the respective chamber from the respective additional sensor.

In some instances, the system may further comprise a plurality of to-be-tested components. A respective to-be-tested component of the plurality of to-be-tested components may be connected between the pump and the respective valve of the plurality of valves. The respective to-be-tested component may include biomaterial. The respective to-be-tested component may be configured to allow the media flowing through the chamber at least partially contact the biomaterial.

In some instances, the respective to-be-tested component may be an implantable valve.

In some instances, the system may further comprise a user interface, configured to present information.

In some instances, the system may further comprise a plurality of on/off switches. A respective on/off switch may be configured to turn on/off the respective chamber.

In some instances, the system may further comprise a plurality of actuators. A respective actuator may be electrically connected between the FLO and the respective valves. The respective actuator may be configured to drive the respective valve.

In some instances, the FLO may be further configured to send a pump signal to the pump to set a status of the pump; receive the respective monitoring parameter associated with the respective chamber from the respective sensor; determine whether the respective monitoring parameter associated with the respective chamber is higher than a respective threshold; send a first driving signal to the respective actuator to drive the respective valve in a first direction upon determining that the respective monitoring parameter associated with the respective chamber is higher than the respective threshold; and/or send a second driving signal to the respective actuator to drive the respective valve in a second direction upon determining that the respective monitoring parameter associated with the respective chamber is lower than the respective threshold. The second direction may be different from the first direction.

In some instances, the respective threshold may be a function of time.

In some instances, the monitoring parameter may include at least one of a pressure of the media flowing through the respective chamber, a flow rate of the media flowing through the respective chamber, a waveform of the pressure of the media flowing through the respective chamber, and/or a waveform of the flow rate of the media flowing through the respective chamber.

In some instances, the respective monitoring parameter may be a function of time.

In some instances, the one or more controllable parameters associated with the respective chamber may include a pressure of the media flowing through the respective chamber, a flow rate of the media flowing through the respective chamber, an amplitude of a waveform of the flow rate of the media flowing through the respective chamber, a frequency of the waveform of the flow rate of the media flowing through the respective chamber, an amplitude of a waveform of the pressure of the media flowing through the respective chamber, a frequency of the waveform of the pressure of the media flowing through the respective chamber, and a resistance of the media flowing through the respective chamber.

In some instances, the unit of the flow rate of the media flowing through the respective chamber may be ml/hr. The unit of the amplitude of the waveform of the flow rate of the media flowing through the respective chamber may be Δflow rate/Δtime. The unit of the frequency of the waveform of the flow rate of the media flowing through the respective chamber may be Hertz. The unit of an amplitude of the waveform of the pressure of the media flowing through the respective chamber may be mmHg. The unit of the frequency of the waveform of the pressure of the media flowing through the respective chamber may be Hertz. The unit of the resistance of the media flowing through the respective chamber may be mmHg*hr*ml^-1.

In some instances, the FLO may be further configured to communicate with a network.

In some instances, the respective chamber may be detachable from the system.

In some instances, the respective chamber may be a compliance chamber.

In some instances, the respective chamber may be configured to allow the media containing biomaterial to flow through.

Another aspect of this disclosure provides a method for modeling fluid flow. The method may comprise the following. A pump signal may be sent to a pump to set a status of the pump. The pump may be connected to a respective primary end of a respective chamber of a plurality of chambers. The pump may be configured to move media to or from the respective chamber. A respective monitoring parameter associated with the respective chamber may be received from a respective sensor of a plurality of sensors. The respective sensor may be connected to a respective primary end or a secondary end of the respective chamber. The respective sensor may be configured to sense the respective monitoring parameter associated with the respective chamber. The respective chamber may be independently controlled, where one or more controllable parameters associated with the respective chamber may be manipulated based on the respective monitoring parameter associated with the respective chamber.

In some instances, independently controlling the respective chamber may comprise the following. Whether the respective monitoring parameter associated with the respective chamber is higher than a respective threshold may be determined. A first driving signal may be sent to a respective actuator of a plurality of actuators to drive the respective valve of a plurality of valves in a first direction upon determining that the respective monitoring parameter associated with the respective chamber is higher than the respective threshold. The respective valve may be connected to the respective secondary end or the primary end of the respective chamber. The respective valve may be configured to control a fluid velocity of the media flowing through the respective chamber. Additionally or alternatively, a second driving signal may be sent to the respective actuator to drive the respective valve in a second direction upon determining that the respective monitoring parameter associated with the respective chamber is lower than the respective threshold. The second direction may be different from the first direction.

In some instances, the respective monitoring parameter may be a function of time, and the respective threshold may be a function of time.

In some instances, the method may further comprise the following. A respective additional parameter may be received from a respective additional sensor of a plurality of additional sensors. The respective additional sensor may be connected to the respective secondary end or the primary end of the respective chamber. The respective additional sensor may be configured to sense the respective additional parameter associated with the respective chamber.

In some instances, the method may further comprise the following. Data associated with the respective chamber may be stored in a storage component.

In some instances, the method may further comprise the following. Information may be presented on a user interface.

In some instances, the method may further comprise the following. A respective input may be received via a respective on/off switch of a plurality of on/off switches. The respective chamber may be turned on/off based on the respective input.

Yet another aspect of this disclosure provides a computer-readable medium storing computer-readable instructions executable by one or more processors, that when executed by the one or more processors, causes the one or more processors to perform acts comprising the following. A pump signal may be sent to a pump to set a status of the pump. The pump may be connected to a respective primary end of a respective chamber of a plurality of chambers. The pump may be configured to move media to or from the respective chamber. A respective monitoring parameter associated with the respective chamber may be received from a respective sensor of a plurality of sensors. The respective sensor may be connected to a respective primary end or a secondary end of the respective chamber. The respective sensor may be configured to sense the respective monitoring parameter associated with the respective chamber. The respective chamber may be independently controlled, where one or more controllable parameters associated with the respective chamber may be manipulated based on the respective monitoring parameter associated with the respective chamber.

In some instances, independently controlling the respective chamber may comprise the following. Whether the respective monitoring parameter associated with the respective chamber is higher than a respective threshold may be determined. A first driving signal may be sent to a respective actuator of a plurality of actuators to drive the respective valve of a plurality of valves in a first direction upon determining that the respective monitoring parameter associated with the respective chamber is higher than the respective threshold. The respective valve may be connected to the respective secondary end or the primary end of the respective chamber. The respective valve may be configured to control a fluid velocity of the media flowing through the respective chamber. Additionally or alternatively, a second driving signal may be sent to the respective actuator to drive the respective valve in a second direction upon determining that the respective monitoring parameter associated with the respective chamber is lower than the respective threshold. The second direction may be different from the first direction.

In some instances, the respective monitoring parameter may be a function of time, and the respective threshold may be a function of time.

In some instances, the acts may further comprise the following. A respective additional parameter may be received from a respective additional sensor of a plurality of additional sensors. The respective additional sensor may be connected to the respective secondary end or the respective primary end of the respective chamber. The respective additional sensor may be configured to sense the respective additional parameter associated with the respective chamber.

In some instances, the acts may further comprise the following. Data associated with the respective chamber may be stored in a storage component.

In some instances, the acts may further comprise the following. Information may be presented on a user interface.

In some instances, the acts may further comprise the following. A respective input may be received via a respective on/off switch of a plurality of on/off switches. The respective chamber may be turned on/off based on the respective input.

Yet another aspect of this disclosure provides an apparatus for modeling fluid flow. The apparatus may comprise one or more processors, memory, coupled to the one or more processors, the memory storing thereon computer-executable modules, executable by the one or more processors. The computer-executable modules may include the following. A pump control module may be configured to send a pump signal to a pump to set a status of the pump. The pump may be connected to a respective primary end of a respective chamber of a plurality of chambers. The pump may be configured to move media to or from the respective chamber. A monitoring parameter receiving module may be configured to receive a respective monitoring parameter associated with the respective chamber from a respective sensor of a plurality of sensors. The respective sensor may be connected to a respective primary end or a secondary end of the respective chamber. The respective sensor may be configured to sense the respective monitoring parameter associated with the respective chamber. A control module may be configured to independently control the respective chamber by manipulating one or more controllable parameters associated with the respective chamber based on the respective monitoring parameter associated with the respective chamber.

In some instances, the control module may be further configured to determine whether the respective monitoring parameter associated with the respective chamber is higher than a respective threshold; send a first driving signal to a respective actuator of a plurality of actuators to drive the respective valve of a plurality of valves in a first direction upon determining that the respective monitoring parameter associated with the respective chamber is higher than the respective threshold; and/or send a second driving signal to the respective actuator to drive the respective valve in a second direction upon determining that the respective monitoring parameter associated with the respective chamber is lower than the respective threshold. The respective valve may be connected to the respective secondary end or the primary end of the respective chamber. The respective valve may be configured to control a fluid velocity of the media flowing through the respective chamber. The second direction may be different from the first direction.

In some instances, the respective monitoring parameter may be a function of time, and the respective threshold may be a function of time.

Techniques discussed herein may provide improvements to in vitro systems for modeling fluid flow. The improvements may include one or more of: controlling pump(s) and valves to manipulate one or more controllable parameters of the media flowing through the chamber; driving valves via actuators to control the media flowing through the chamber; manipulating the one or more controllable parameters of the media with a function of time; manipulating the pressure of the media by controlling the resistance of the media flowing through the chamber using valves (for instance, without employing headspace gases to increase or decrease pressure in the system); manipulating the flow rate and/or the pressure of the media in order to mimic multiple different flow rate waveforms and pressure waveforms over a period of time; running multiple chambers with different conditions in parallel; providing scalability/configurability of the system; and/or employing single-stage compliance chambers without air pockets.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1A:
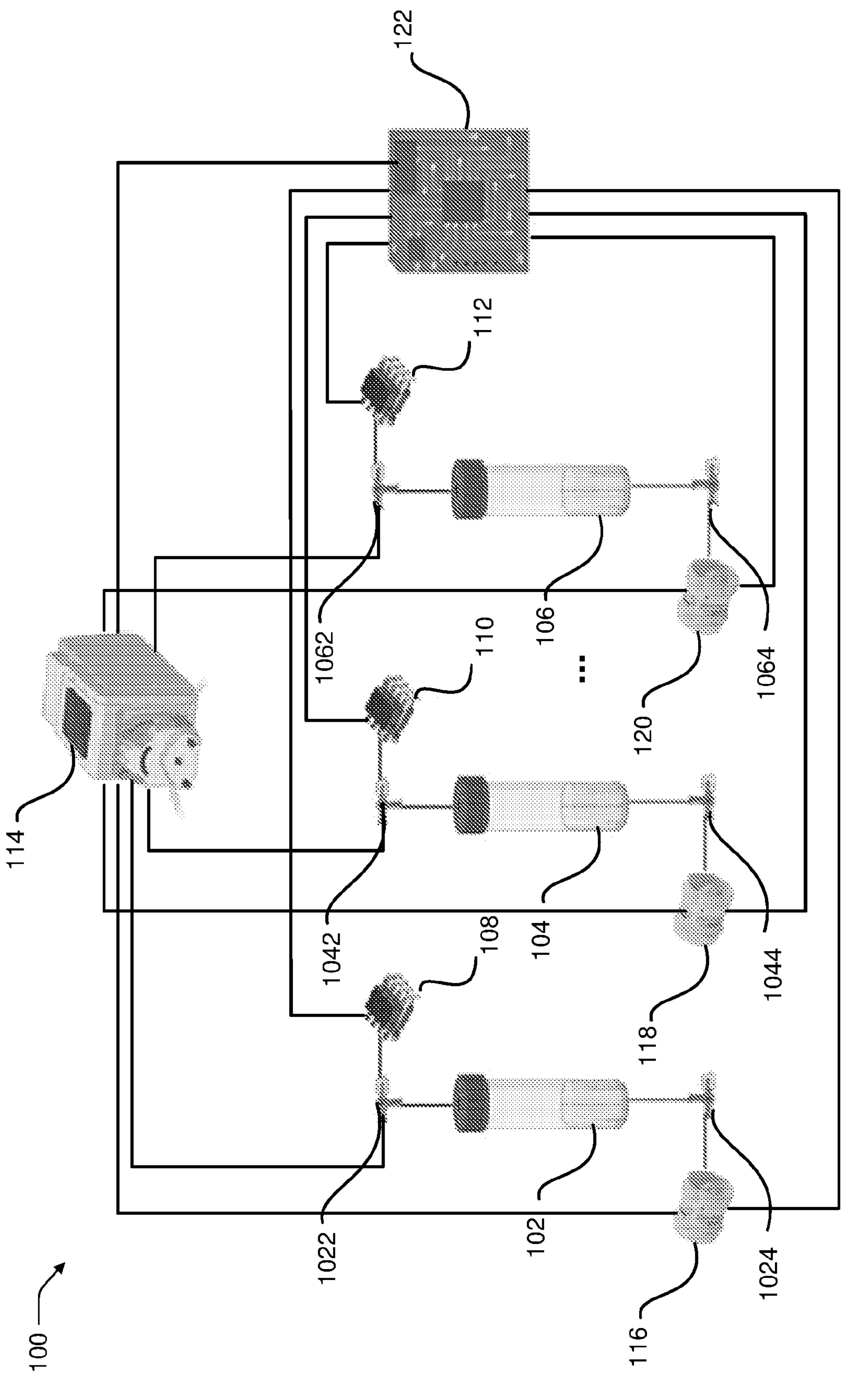
FIG. 1A and FIG. 1B illustrate an exemplary system for modeling fluid flow according to implementations of this disclosure.

Disclosed herein are implementations of systems, methods, apparatuses, and computer-readable media for modeling fluid flow, that may monitor and control one or more controllable parameters, such as volumetric flow rate, pressure, flow amplitude of a desired fluid/media, for instance in a fluid management device such as a bioreactor. In exemplary aspects, the desired fluid simulates a physiologic fluid, such as cerebrospinal fluid, blood or a blood faction (such as plasma or serum), lymph, urine, saliva, synovial fluid, vitreous fluid, interstitial fluid, amniotic fluid, and so forth; or a synthetic physiologic fluid or supplement (such as, for instance, a blood substitute).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials is individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

Throughout this disclosure, the pressure may also be referred to as the bulk pressure and the volumetric pressure.

The flow rate may also be referred to as bulk flow rate and volumetric flow rate. The unit mmHg may refer to millimeters of mercury. The unit of ml/hr may refer to milliliter per hour. The parameters discussed may include the bulk pressure, the waveform of the pressure, the bulk flow rate, the flow rate waveform that can include compliance of the chamber, etc.

Figure 1B:
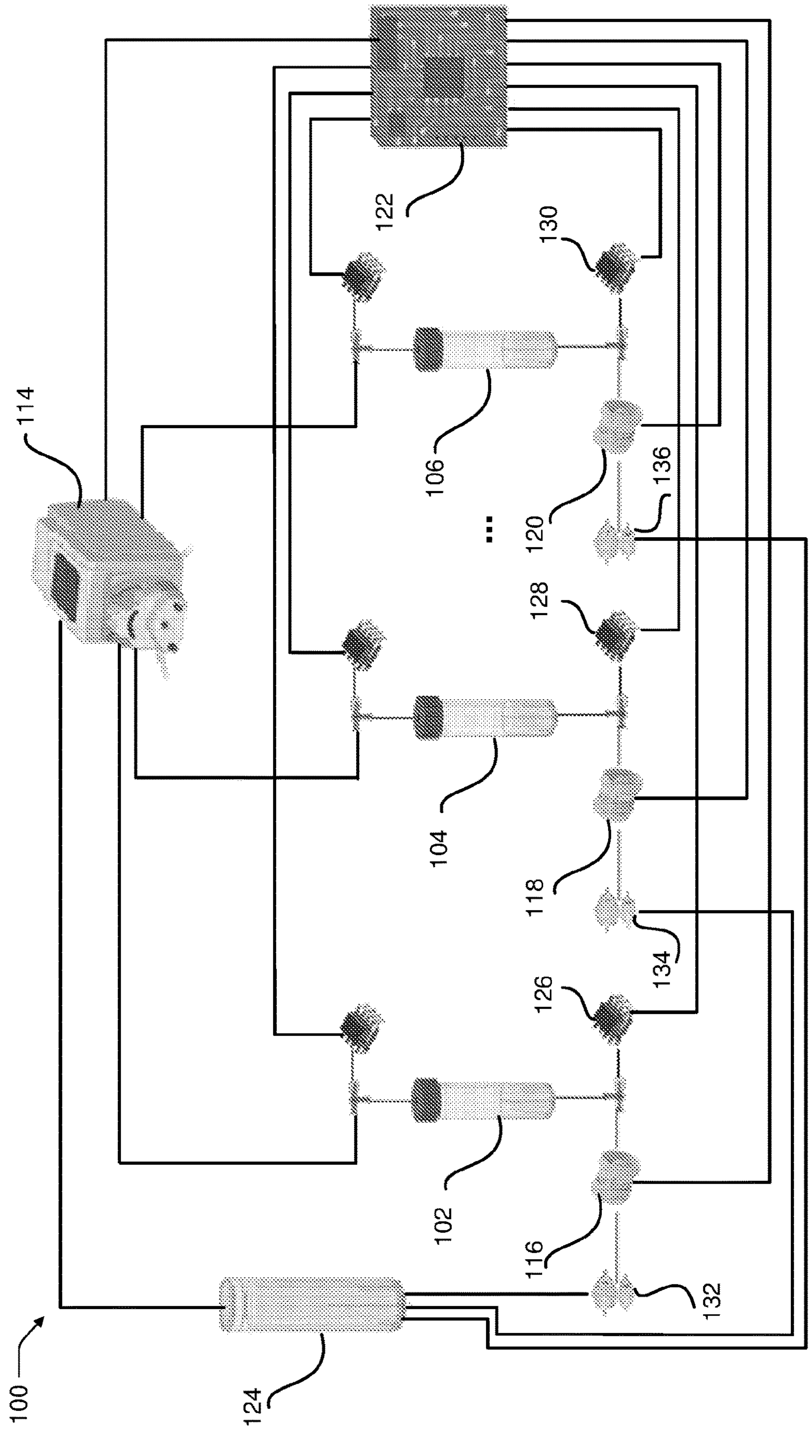

FIG. 1A and FIG. 1B illustrate an exemplary system 100 for modeling fluid flow according to implementations of this disclosure. In implementations, the system 100 may be a pulsatile flow system, a syringe flow system, or any other fluid flow systems. This disclosure is not limited thereto.

Referring to FIG. 1A, the system 100 may include a plurality of chambers (102, 104, 106), a plurality of sensors (108, 110, 112), a pump 114, a plurality of valves (116, 118, 120), an FLO 122.

In implementations, the plurality of chambers may include a first chamber 102, a second chamber 104, . . . , and an nth chamber 106. N may be a positive integer. The system 100 may be multiplexing and provide high throughput, for instance, capable of running multiple (such as more than 4, more than 8, more than 12, more than 16, and the like) chambers in parallel. In implementations, the system 100 is scalable/configurable in terms of the chamber numbers. In implementations, condition(s) such as flow rate, pressure and so on in two or more of the parallel chambers can be independently controlled.

A respective chamber of the plurality of chambers may have a respective primary end and a respective secondary end. For example, the first chamber 102 may have a first primary end 1022 and a first secondary end 1024. The second chamber 104 may have a second primary end 1042 and a second secondary end 1044. The nth chamber 106 may have an nth primary end 1062 and an nth secondary end 1064. The terms “primary end” and “secondary end” are example names to refer to different ends of the chamber and this disclosure is not limited thereto.

In implementations, the chambers may be compliance chambers. As an example, the chambers may be single-stage compliance chambers. This disclosure is not limited thereto.

In implementations, the respective chamber may be configured to allow the media containing biomaterial to flow through.

In implementations, the primary end may be the inlet of the chamber, while the secondary end may be the outlet of the chamber. Alternatively, the primary end may be the outlet of the chamber, while the secondary end may be the inlet of the chamber. This disclosure is not limited thereto.

In implementations, the respective chamber may be imageable. For example, the respective chamber may be a 360-degree imageable in situ chamber composed of a substantially transparent component base, such as a component comprising one or more of vinyl, nylon, or silicone. By way of further example, the following provides a list of material sheets that can be used and why they are considered useful or beneficial: Teflon (biocompatible, flexible, and has good structural integrity over time); Silicone (very biocompatible, flexible, readily available in multiple thicknesses, translucent, and can form watertight seals with many materials); PVC (relatively low cost, great for imaging the chambers); and Nylon (available in various thicknesses, very chemically stable, low cost, transparent, easy for imaging).

In implementations, the respective chamber (102, 104, 106) may be detachable from other parts of the system 100 and restorable into the system 100. For example, the first chamber 102 may be detachable from other parts of the system 100 and restorable into the system 100. The second chamber 104 may be detachable from other parts of the system 100 and restorable into the system 100. The nth chamber 106 may be detachable from other parts of the system 100 and restorable into the system 100. The respective chamber may be placed into a carrying case in which the respective chamber may be detached from other parts of the system 100 and imaged. Furthermore, the respective chamber may be restored back into the system 100 after imaged. In implementations, the carrying case may be produced by custom 3D printing, or any other suitable procedures. This disclosure is not limited thereto.

In implementations, the 360-degree imageable chamber together with the sample/media inside may be detached from other parts of the system and imaged. Moreover, the 360-degree imageable chamber may be restored into the system after being imaged. By using a flexible/detachable chamber that is 360-degree imageable, the chamber is still intact and in a sterile environment for experiments to continue after being imaged.

In implementations, the plurality of sensors may include a first sensor 108, a second sensor 110, . . . , and an nth sensor 112. A respective sensor of the plurality of sensors may be connected to the respective primary end and/or the secondary end of the respective chamber. For example, the first sensor 108 may be connected to the first primary end 1022 of the first chamber 102. The second sensor 110 may be connected to the second primary end 1042 of the second chamber 104. The nth sensor 112 may be connected to the nth primary end 1062 of the nth chamber 106. Additionally or alternatively, the first sensor 108, the second sensor 110, . . . , and the nth sensor 112 may be connected to the secondary ends of the chambers.

In implementations, the respective sensor may be configured to sense a respective monitoring parameter associated with the respective chamber. For example, the first sensor 108 may be configured to sense the first monitoring parameter associated with the first chamber 102. The second sensor 110 may be configured to sense the second monitoring parameter associated with the second chamber 104. The nth sensor 112 may be configured to sense the nth monitoring parameter associated with the nth chamber 106.

In implementations, the monitoring parameter may be the pressure of the media flowing through the respective chamber, the flow rate of the media flowing through the respective chamber, the waveform of the pressure of the media flowing through the respective chamber, the waveform of the flow rate of the media flowing through the respective chamber, etc. This disclosure is not limited thereto. Throughout this disclosure, the pressure may also be referred to as the bulk pressure and the volumetric pressure. Throughout this disclosure, the flow rate may also be referred to as bulk flow rate and volumetric flow rate.

In implementations, the monitoring parameter may be a function of time.

In implementations, the pump 114 may be connected to the respective primary end of the respective chamber, for example, via tubing. For example, the pump 114 may be connected to the first primary end 1022 of the first chamber 102 via tubing. The pump 114 may be connected to the second primary end 1042 of the second chamber 104 via tubing. The pump 114 may be connected to the nth primary end 1062 of the nth chamber 106 via tubing. In implementations, the pump 114 may be a pulsatile pump or any other suitable pump. This disclosure is not limited thereto.

In implementations, the pump 114 may be configured to move media/fluid to or from the respective chamber, for example, via tubing, separately. For example, the pump 114 may be configured to move media to different chambers with different speeds/flow rates. In implementations, additional cell stimuli, including various cytokines, can be added to the media to mimic biomaterial insertion, cell-cell communication, and cell activation. Additionally or alternatively, more than one pumps may be provided in the system 100 to drive the media to the chambers.

In implementations, the pump 114 may be configured to move the media in a way simulating human's pulsation of the heartbeat. For example, the pulsations may be generated by the rotor movements on the pump 114.

In implementations, the plurality of valves may include a first valve 116, a second valve 118, . . . , and an nth valve 120. N may be a positive integer. A respective valve of the plurality of valves may be connected to the respective secondary end or the respective primary end of the respective chamber. For example, the first valve 116 may be connected to the first secondary end 1024 of the first chamber 102. The second valve 118 may be connected to the second secondary end 1044 of the second chamber 104. The nth valve 120 may be connected to the nth secondary end 1064 of the nth chamber 106. Additionally or alternatively, the first valve 116, the second valve 118, . . . , and the nth valve 120 may be connected to the primary ends of the chambers. In implementations, the first valve 116, the second valve 118, . . . , and the nth valve 120 may be variable valves. This disclosure is not limited thereto.

In implementations, the valves may be variable valves or any suitable types of valves. This disclosure is not limited thereto.

In implementations, the respective valve may be configured to control a fluid velocity of the media flowing through the respective chamber. For example, the first valve 116 may be configured to control the fluid velocity of the media flowing through the first chamber 102. The second valve 118 may be configured to control the fluid velocity of the media flowing through the second chamber 104. The nth valve 120 may be configured to control the fluid velocity of the media flowing through the nth chamber 106.

In implementations, the FLO 122 may be electrically connected to the plurality of sensors (108, 110, 112), the pump 114, and the plurality of valves (116, 118, 120). For example, the FLO 122 may be electrically connected to the first sensor 108. The FLO 122 may be electrically connected to the second sensor 110. The FLO 122 may be electrically connected to the nth sensor 112. The FLO 122 may be electrically connected to the first valve 116. The FLO 122 may be electrically connected to the second valve 118. The FLO 122 may be electrically connected to the nth valve 120.

In implementations, the FLO may be configured to receive the respective monitoring parameter from the respective sensor. For example, the FLO 122 may be configured to receive the first monitoring parameter associated with the first chamber 102 from the first sensor 108. The FLO 122 may be configured to receive the second monitoring parameter associated with the second chamber 104 from the second sensor 110. The FLO 122 may be configured to receive the nth monitoring parameter associated with the nth chamber 106 from the nth sensor 112.

In implementations, the FLO 122 may be configured to independently/individually control the respective chamber by manipulating/regulating one or more controllable parameters associated with the respective chamber based on the respective monitoring parameter associated with the respective chamber.

In implementations, the one or more controllable parameters associated with the respective chamber may include a pressure of the media flowing through the respective chamber, a flow rate of the media flowing through the respective chamber, an amplitude of a waveform of the flow rate of the media flowing through the respective chamber, a frequency of the waveform of the flow rate of the media flowing through the respective chamber, an amplitude of a waveform of the pressure of the media flowing through the respective chamber, a frequency of the waveform of the pressure of the media flowing through the respective chamber, a resistance of the media flowing through the respective chamber, the compliance of the respective chamber, etc. This disclosure is not limited thereto.

In implementations, the unit of the flow rate of the media flowing through the respective chamber may be ml/hr. The unit of the amplitude of the waveform of the flow rate of the media flowing through the respective chamber may be Δflow rate/Δtime. The unit of the frequency of the waveform of the flow rate of the media flowing through the respective chamber may be Hertz. The unit of an amplitude of the waveform of the pressure of the media flowing through the respective chamber may be mmHg. The unit of the frequency of the waveform of the pressure of the media flowing through the respective chamber may be Hertz. The unit of the resistance of the media flowing through the respective chamber may be mmHg*hr*ml^-1.

In implementations, the system 100 may further include a plurality of actuators (not shown). A respective actuator may be electrically connected between the FLO 122 and the respective valve. The respective actuator may be configured to drive the respective valve. For example, a first actuator (not shown) may be electrically connected between the FLO 122 and the first valve 116. A second actuator (not shown) may be electrically connected between the FLO 122 and the second valve 118. An nth actuator (not shown) may be electrically connected between the FLO 122 and the nth valve 120.

In implementations, the actuators may be stepper motors or any suitable mechanisms that can drive the valves. This disclosure is not limited thereto.

In implementations, the FLO 122 may be configured to send a pump signal to the pump 114 to set a status of the pump 114; receive the respective monitoring parameter associated with the respective chamber from the respective sensor; and determine whether the respective monitoring parameter associated with the respective chamber is higher than a respective threshold. The FLO 122 may be configured to send a first driving signal to the respective actuator to drive the respective valve in a first direction upon determining that the respective monitoring parameter associated with the respective chamber is higher than the respective threshold; and/or send a second driving signal to the respective actuator to drive the respective valve in a second direction upon determining that the respective monitoring parameter associated with the respective chamber is lower than the respective threshold.

In implementations, the first direction and the second direction may be different from/opposite to each other. For example, the first direction may be clockwise, while the second direction may be counterclockwise. As another example, the first direction may be counterclockwise, while the second direction may be clockwise. As yet another example, the first direction may be from left to right, while the second direction may be from right to left, and vice versa.

In implementations, driving the respective valve in the first direction or the second direction may have different/opposite effects on the media flowing through the respective chamber. For example, driving the respective valve in the first direction may increase the resistance to the media, while driving the valves in the second direction may decrease the resistance to the media. Additionally or alternatively, driving the valves in the first direction may decrease the resistance to the media, while driving the valves in the second direction may increase the resistance to the media.

As another example, driving the respective valve in the first direction may increase the local speed/flow rate of the media, while driving the valves in the second direction may decrease the local speed/flow rate of the media. Additionally or alternatively, driving the valves in the first direction may decrease the local speed/flow rate of the media, while driving the valves in the second direction may increase the local speed/flow rate of to the media.

In implementations, by driving the respective valve connected to the respective secondary end of the respective chamber in the first direction or the second direction, the respective monitoring parameter (such as the pressure of the media flowing through the respective chamber, the flow rate of the media flowing through the respective chamber, the waveform of the pressure of the media flowing through the respective chamber, the waveform of the flow rate of the media flowing through the respective chamber, and the like) at the respective primary end of the respective chamber may be manipulated. For example, the respective valve may be driven to increase/decrease the resistance to the media flowing through the chamber thereby changing the inline pressure of the chamber while leaving the volumetric flow rate of the media the same/unchanged.

For example, the FLO 122 may be configured to determine whether the first monitoring parameter associated with the first chamber 102 is higher than a first threshold. The FLO 122 may be configured to send a first driving signal to the first actuator to drive the first valve 116 in a first direction upon determining that the first monitoring parameter associated with the first chamber 102 is higher than the first threshold; and/or send a second driving signal to the first actuator to drive the first valve 116 in a second direction upon determining that the first monitoring parameter associated with the first chamber 102 is lower than the first threshold.

For example, the FLO 122 may be configured to determine whether the second monitoring parameter associated with the second chamber 104 is higher than a second threshold. The FLO 122 may be configured to send a first driving signal to the second actuator to drive the second valve 118 in a first direction upon determining that the second monitoring parameter associated with the second chamber 104 is higher than the second threshold; and/or send a second driving signal to the second actuator to drive the second valve 118 in a second direction upon determining that the second monitoring parameter associated with the second chamber 104 is lower than the second threshold.

For example, the FLO 122 may be configured to determine whether the nth monitoring parameter associated with the nth chamber 106 is higher than an nth threshold. The FLO 122 may be configured to send a first driving signal to the nth actuator to drive the nth valve 120 in a first direction upon determining that the nth monitoring parameter associated with the nth chamber 106 is higher than the nth threshold; and/or send a second driving signal to the nth actuator to drive the nth valve 120 in a second direction upon determining that the nth monitoring parameter associated with the nth chamber 106 is lower than the nth threshold.

In implementations, the respective threshold (the first threshold, the second threshold, . . . the nth threshold) may be a function of time. Alternatively, the respective threshold may be a constant value. This disclosure is not limited thereto.

For example, the respective threshold may be a function of time that fabricates waveform functions over time, for instance, in order to match mean results of population or a specific patient.

By way of example, the respective threshold may be a function of time that mimics the pressures, flow rates, and pressure amplitudes seen in the brain. Parameters related to the brain may include 17 mmHg average pressure, 6-9 mmHg for pressure amplitudes, and 15-30 ml/hr flow rate. The values are chosen to mimic parameters that are significant in brain physiology and pathophysiology. While the brain is used as the example model organ, any waveform can be programmed into the threshold. The system 100 may be applicable to any other organ systems such as the heart, kidneys, and liver.

In implementations, different thresholds may be set for different chambers. Multiple chambers may run in parallel with different thresholds.

The system 100 may run for an extended period, such as more than seven days, at least two weeks, at least three weeks, at least four weeks, more than four weeks, at least a month, more than a month, or more than two months. This disclosure is not limited thereto.

In implementations, the system 100 may include a user interface (not shown). The user interface may include a display or multiple displays. For example, the display may be an organic light-emitting diode (OLED) display, a touch screen, or any other suitable type of displays. The user interface may further include an input device (such as a mouse, a keyboard, a voice input device and the like), a speaker, a microphone, and so on. This disclosure is not limited thereto.

In implementations, the user interface may be configured to present information. For example, the user interface may present instructions allowing the user to set the flow rate/speed of pump, the number of the chambers, turn on/off a respective chamber, etc. The user interface may present data/graphs associated with the respective chamber. The user interface may present warning signals, such as when the storage components are no longer connected or when a chamber is inactive.

In implementations, the system 100 may include a plurality of on/off switches (not shown). A respective on/off switch may be configured to turn on/off the respective chamber.

In implementations, the system 100/FLO 122 may be configured to communicate with a network, such as a Wi-Fi network, a cellular network, a wired network, and so on. This disclosure is not limited thereto.

In implementations, the system 100 may be scalable/configurable. The number of components such as chambers, valves, actuators, sensors may be scaled/configured to adapt to actual needs. For example, additional chambers, valves, actuators, sensors, etc. may be added to expand the capacity of the system 100. Additionally or alternatively, some of the chambers, valves, actuators, sensors, etc. may be detached from the system 100 to make the system 100 compact.

Referring to FIG. 1B, the system 100 may further include a reservoir 124, a plurality of additional sensors (126, 128, 130), and a plurality of to-be-tested components (132, 134, 136).

In implementations, the reservoir 124 may be connected between the pump 114 and the respective valve. For example, the reservoir 124 may be connected between the pump 114 and the first valve 116. The reservoir 124 may be connected between the pump 114 and the second valve 118. The reservoir 124 may be connected between the pump 114 and the nth valve 120.

In implementations, the reservoir may be configured to contain the media. Additionally, or alternatively, though FIG. 1B shows one reservoir, the system 100 may include multiple reservoirs. This disclosure is not limited thereto.

In implementations, the plurality of additional sensors may include a first additional sensor 126, a second additional sensor 128, . . . , and an nth additional sensor 130. The respective additional sensor may be connected to the respective secondary end of the respective chamber, for example, via an air column. The respective additional sensor may be configured to sense a respective additional parameter associated with the respective chamber. For example, the first additional sensor 126 may be configured to sense the additional parameter associated with the first chamber 102. The second additional sensor 128 may be configured to sense the additional parameter associated with the second chamber 104. The nth additional sensor 130 may be configured to sense the additional parameter associated with the nth chamber 106.

In implementations, the additional parameter may be the pressure of the media flowing through the respective chamber, the flow rate of the media flowing through the respective chamber, etc. This disclosure is not limited thereto.

For example, if the secondary end is the outlet of the chamber, the additional sensor may be used to sense the parameter representative of downstream collection.

In implementations, the FLO 122 may be configured to be electrically connected to the plurality of additional sensors. For example, the FLO 122 may be configured to be electrically connected to the first additional sensor 126. The FLO 122 may be configured to be electrically connected to the second additional sensor 128. The FLO 122 may be configured to be electrically connected to the nth additional sensor 130.

In implementations, the FLO 122 may be configured to receive the respective additional parameter associated with the respective chamber from the respective additional sensor. For example, the FLO 122 may be configured to receive the additional parameter associated with the first chamber 102. The FLO 122 may be configured to receive the additional parameter associated with the second chamber 104. The FLO 122 may be configured to receive the additional parameter associated with the nth chamber 106.

In implementations, the plurality of to-be-tested components may include a first to-be-tested component 132, a second to-be-tested component 134, . . . , and an nth to-be-tested component 136. A respective to-be-tested component of the plurality of to-be-tested components may be connected between the pump 114/reservoir 124 and the respective valve of the plurality of valves. For example, the first to-be-tested component 132 may be connected between the pump 114/reservoir 124 and the first valve 116. The second to-be-tested component 134 may be connected between the pump 114/reservoir 124 and the second valve 118. The nth to-be-tested component 136 may be connected between the pump 114/reservoir 124 and the nth valve 120.

In implementations, the first to-be-tested component 132, the second to-be-tested component 134, . . . , and the nth to-be-tested component 136 may include biomaterial. The respective to-be-tested component may be configured to allow the media flowing through the chamber at least partially contact the biomaterial. The first to-be-tested component 132, the second to-be-tested component 134, . . . , and the nth to-be-tested component 136 may be optional.

In implementations, the respective to-be-tested component may include any types of biomaterials such as brain shunts, pacemakers, heart valves, orthopedic devices, prosthesis, artificial vessels, and so on. As an example, the respective to-be-tested component may be an implantable valve. The implantable valve may open/close at specific pressures.

In implementations, the respective additionally sensor (126, 128, 130) may be configured to sense parameters associated with the respective to-be-tested component (132, 134, 136).

With the system 100, in vitro systems for modeling fluid flow (such as a bioreactor) may be improved. By way of example, the biological cell or tissue may contact the media within the system for modeling fluid flow. The flow amplitude of media in contact with the biological cell or tissue may be changed. The response of the biological cell or tissue during or after the change of the media flow amplitude may be observed and/or measured. Optionally, one or more characteristics of the response may be recorded in a non-transitory computer readable medium.

By way of another example, a test compound for effect(s) on a biological cell or tissue may be screened. The biological cell or tissue may contact a medium comprising the test compound within the system for modeling fluid flow. The flow amplitude of the media in contact with the biological cell or tissue may be changed. A response of the biological cell or tissue during or after the change of the flow amplitude may be observed and/or measured. Optionally, one or more characteristics of the response may be recorded in a non-transitory computer readable medium.

The system 100 may be a computer-based bioreactor system including devices, software, and non-computer-based chambers. The computer-based bioreactor system can create a more physiologic environment over a longer period than conventional systems, and is useful to test biomaterials. The computer-based bioreactor system may model both flow rate and pressure at physiologic conditions, which enables better study of organ systems, cells, and tissues. An exemplary bioreactor may independently control multiple (such as more than 12, more than 15, more than 18, more than 20, or more than 24) chambers; integrate live cells/gel matrix into each sample; control flow/pressure within each chamber; and provide/measure multiple flow/pressure waveforms daily/weekly/monthly.

The system 100 may create a high throughput, long-term, physiologically similar system in which biomaterials can be effectively tested. The system 100 may create a more accurate environment in which biomaterials can be tested before human trials. The system 100 may reduce the cost of biomaterial development as more variables seen in vivo will be accounted for in the FLO, including but not limited to compliance, flow rate, and pressure. Additionally, given the high throughput and programmable nature of the FLO, patient data can be programmed to run the test, and specific treatment reactions can be better predicted before implantation.

The system 100 may provide improvements to in vitro systems for modeling fluid flow. The improvements may include one or more of: controlling pump(s) and valves to manipulate one or more controllable parameters of the media flowing through the chamber; driving valves via actuators to control the media flowing through the chamber; manipulating the one or more controllable parameters of the media with a function of time; manipulating the pressure of the media by controlling the resistance of the media flowing through the chamber using valves (for instance, without employing headspace gases to increase or decrease pressure in the system); manipulating the flow rate and/or the pressure of the media in order to mimic multiple different flow rate waveforms and pressure waveforms over a period of time; running multiple chambers with different conditions in parallel; providing scalability/configurability of the system; and/or employing single-stage compliance chambers without air pockets.

Figure 2:
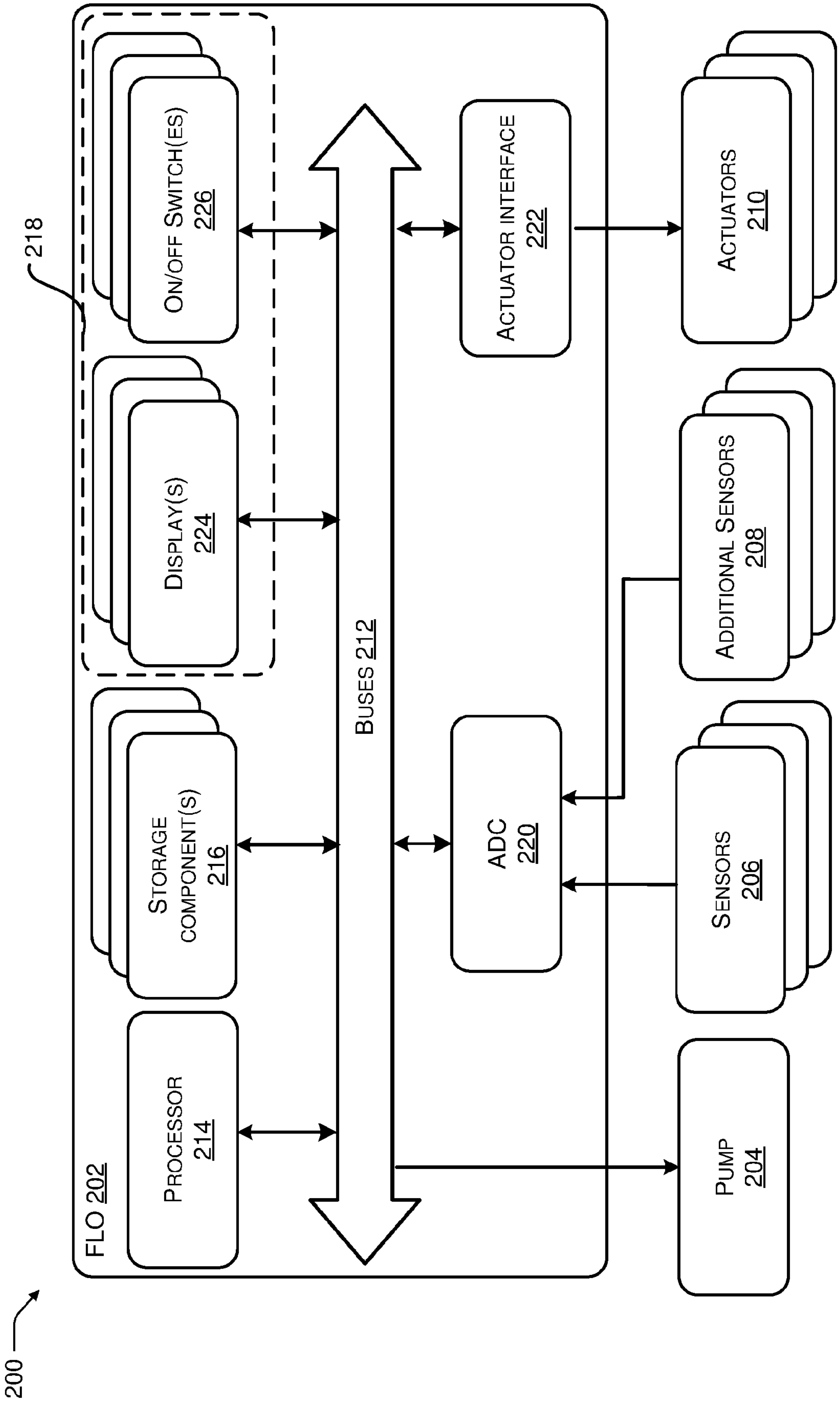
FIG. 2 illustrates an exemplary scenario in which an FLO cooperates with other parts of a system for modeling fluid flow according to implementations of this disclosure.

FIG. 2 illustrates an exemplary scenario 200 in which an FLO 202 cooperates with other parts of a system for modeling fluid flow according to implementations of this disclosure. Additional details of the system for modeling fluid flow are described throughout this disclosure.

Referring to FIG. 2, the scenario 200 shows an FLO 202, a pump 204, a plurality of sensors 206, a plurality of additional sensors 208, and a plurality of actuators 210.

The FLO 202 may include buses 212, a processor 214, one or more storage components 216, an interface 218, an analog to digital converter (ADC) 220, and a actuator interface 222. The interface 218 may include one or more displays 224 and one or more on/off switches 226.

In implementations, the processor 214 may be configured to execute computer-readable instructions to perform methods and acts described throughout this disclosure. The processor 214 may be configured to communicate with the one or more storage components 216, the user interface 218, the ADC 220, and the actuator interface 222 via the buses 212. In implementations, the processor 214 may be a microcontroller (such as a single-core microcontroller, a multicore microcontroller, and the like), an embedded processor, a digital signal processor (DSP), or any suitable types of processors. This disclosure is not limited thereto.

In implementations, the one or more storage components 216 may be configured to store data. In implementations, the one or more storage components 216 may be Secure Digital (SD) cards, or any suitable types of memories. This disclosure is not limited thereto. For example, different data points used to derive the average pressure may be sent to two different SD cards to create the pressure waveform. The FLO 202 may use two pairs of SD cards to ensure that if one pair of SD cards reach the capacity or is disconnected, data can be recovered from a backup pair of SD cards.

In implementations, the user interface 218 may be configured to present information via the one or more displays 224 and interact with the user. For example, the user interface may present instructions on the user interface, allowing the user to set the flow rate/speed of the pump, the number of the chambers, turn on/off a respective chamber, etc. The user interface may present data/graphs associated with a respective chamber of a plurality of chambers. Additional details of the plurality chambers are described throughout this disclosure and are not repeated here.

In implementations, the one or more on/off switches 226 may be configured to turn on/off the plurality of chambers.

In implementations, the ADC 220 may be configured to convert analog (continuous, infinitely variable) signals to digital (discrete-time, discrete-amplitude) signals.

In implementations, the actuator interface 222 may be configured to send signals to the plurality of actuators 210 in a multiplexed way. A set of binary numbers may be sent out from the actuator interface 222 to the plurality of actuators 210 using a defined sequence.

In implementations, the FLO 202 may be configured to send pump signal to the pump 204 to set a status of the pump 204. For example, the status of the pump 204 may include, but is not limited to, the speed of the pump 204, the flow rate of the pump 204, etc. The pump 204 may be connected to a plurality of chambers via tubing. The pump 204 may be configured to move media to or from the respective chamber of the plurality of chambers. Additional details of the pump and the chambers are described throughout this disclosure and are not repeated here.

In implementations, the FLO 202 may be configured to receive data from a plurality of sensors 206 via the ADC 220. Additional details of the plurality of sensors are described throughout this disclosure and are not repeated here.

In implementations, the FLO 202 may be configured to receive data from a plurality of additional sensors 208 via the ADC 220. In implementations, the respective additional sensor may be connected to a respective secondary end of the respective chamber. The respective additional sensor may be configured to sense the respective additional parameter associated with the respective chamber. Additional details of the plurality of additional sensors are described throughout this disclosure and are not repeated here. The plurality of additional sensors may be optional.

In implementations, the FLO 202 may be configured to control the plurality of actuators 210 via the actuator interface 222, so as to control a plurality of valves (not shown). Additional details of the plurality of actuators and the plurality of valves are described throughout this disclosure and are not repeated here.

In implementations, the scenario 200 may further include one or more reservoirs and a plurality of to-be-tested components. Additional details of the reservoir(s) and the to-be-tested components are described throughout this disclosure and are not repeated here.

With the scenario 200, the FLO 202 may provide improvements to in vitro systems for modeling fluid flow. The improvements may include one or more of: controlling pump(s) and valves to manipulate one or more controllable parameters of the media flowing through the chamber; driving valves via actuators to control the media flowing through the chamber; manipulating the one or more controllable parameters of the media with a function of time; manipulating the pressure of the media by controlling the resistance of the media flowing through the chamber using valves (for instance, without employing headspace gases to increase or decrease pressure in the system); manipulating the flow rate and/or the pressure of the media in order to mimic multiple different flow rate waveforms and pressure waveforms over a period of time; running multiple chambers with different conditions in parallel; providing scalability/configurability of the system; and/or employing single-stage compliance chambers without air pockets.

FIG. 3A, FIG. 3B, FIG. 3C, FIG. 3D, FIG. 3E, and FIG. 3F illustrate an exemplary process 300 for modeling fluid flow according to implementations of this disclosure.

Figure 3A:
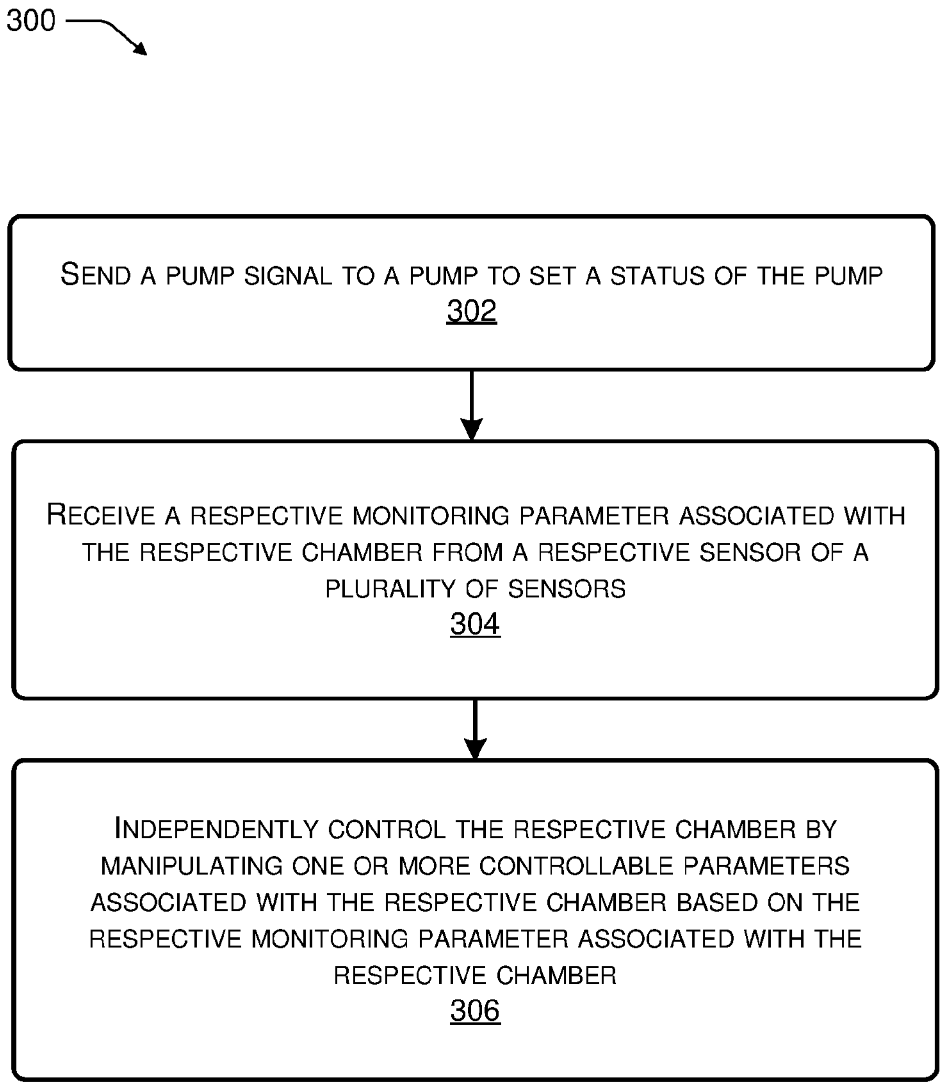
FIG. 3A, FIG. 3B, FIG. 3C, FIG. 3D, FIG. 3E, and FIG. 3F illustrate an exemplary process for modeling fluid flow according to implementations of this disclosure.

Referring to FIG. 3A, the process 300 may include the following.

At block 302, operations may include sending a pump signal to a pump to set a status of the pump. In implementations, the status of the pump may include, but is not limited to, the speed of the pump, the flow rate of the pump, etc. The pump may be connected to a plurality of chambers via tubing. The pump may be configured to move media to or from the respective chamber of the plurality of chambers. Additional details of the pump and the chambers are described throughout this disclosure and are not repeated here.

At block 304, operations may include receiving a respective monitoring parameter associated with the respective chamber from a respective sensor of a plurality of sensors. In implementations, the respective sensor may be connected to a respective primary end or a secondary end of the respective chamber. In implementations, the respective sensor may be configured to sense a respective monitoring parameter associated with the respective chamber. In implementations, the monitoring parameter may be the pressure of the media flowing through the respective chamber, the flow rate of the media flowing through the respective chamber, etc. This disclosure is not limited thereto. Additional details of the sensors are described throughout this disclosure and are not repeated here.

At block 306, operations may include independently controlling the respective chamber by manipulating one or more controllable parameters associated with the respective chamber based on the respective monitoring parameter associated with the respective chamber.

In implementations, the one or more controllable parameters associated with the respective chamber may include a pressure of the media flowing through the respective chamber, a flow rate of the media flowing through the respective chamber, an amplitude of a waveform of the flow rate of the media flowing through the respective chamber, a frequency of the waveform of the flow rate of the media flowing through the respective chamber, an amplitude of a waveform of the pressure of the media flowing through the respective chamber, a frequency of the waveform of the pressure of the media flowing through the respective chamber, and a resistance of the media flowing through the respective chamber, the compliance of the respective chamber, etc. This disclosure is not limited thereto.

In implementations, the unit of the flow rate of the media flowing through the respective chamber may be ml/hr. The unit of the amplitude of the waveform of the flow rate of the media flowing through the respective chamber may be Δflow rate/Δtime. The unit of the frequency of the waveform of the flow rate of the media flowing through the respective chamber may be Hertz. The unit of an amplitude of the waveform of the pressure of the media flowing through the respective chamber may be mmHg. The unit of the frequency of the waveform of the pressure of the media flowing through the respective chamber may be Hertz. The unit of the resistance of the media flowing through the respective chamber may be mmHg*hr*ml^-1.

Additional details of the controllable parameters are described throughout this disclosure and are not repeated here.

Figure 3B:
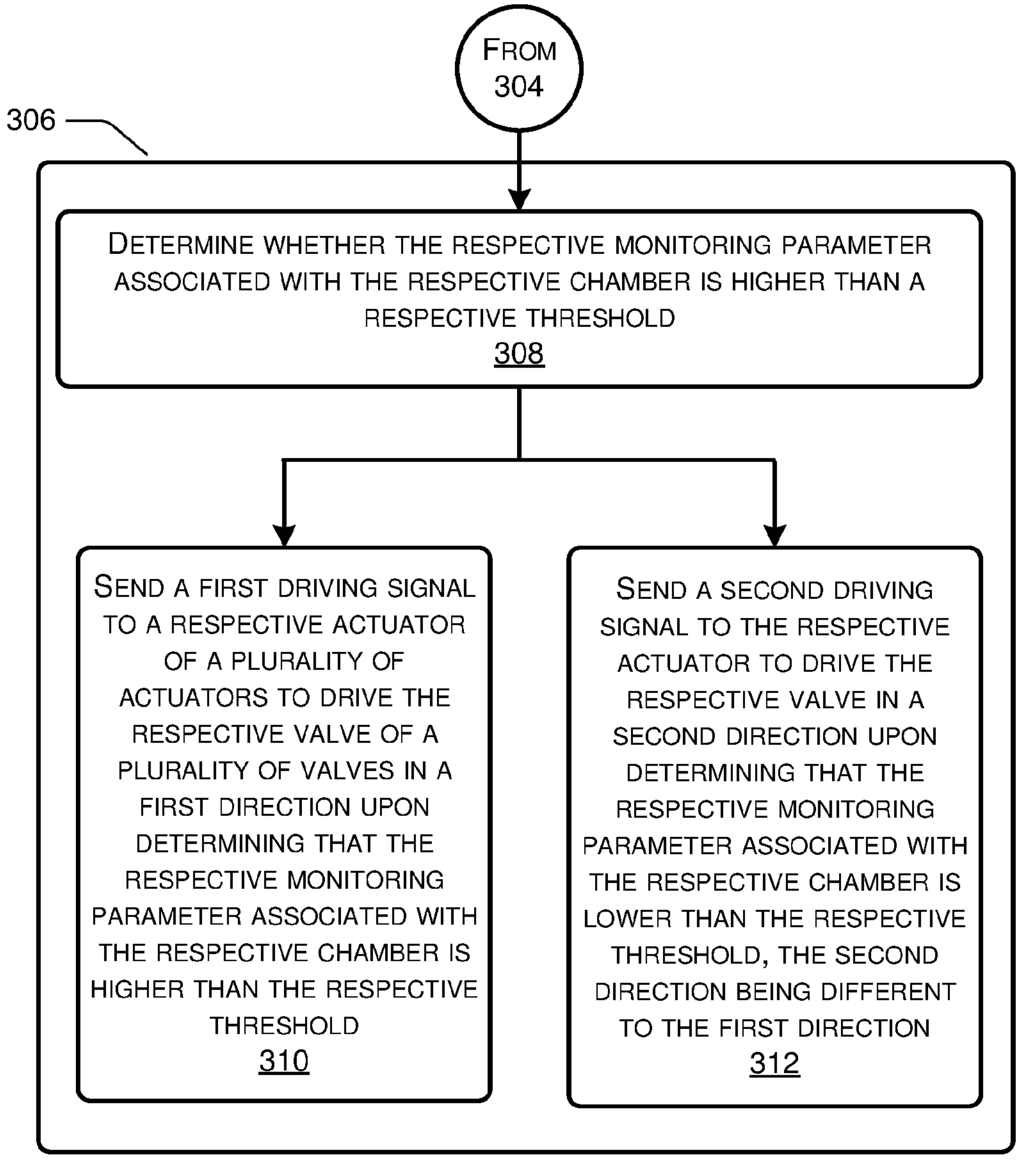

Referring to FIG. 3B, block 306 may include the following.

At block 308, operations may include determining whether the respective monitoring parameter associated with the respective chamber is higher than a respective threshold.

In implementations, the respective threshold may be a function of time. For example, the respective threshold may be a function of time that fabricates any waveform functions over time, for instance, in order to match mean results of population or a specific patient. The process 300 may run for an extended period, such as more than seven days, at least two weeks, at least three weeks, at least four weeks, more than four weeks, at least a month, more than a month, or more than two months. Alternatively, the respective threshold may be a constant value. This disclosure is not limited thereto.

Additional details of the threshold are described throughout this disclosure and are not repeated here.

At block 310, operations may include sending a first driving signal to a respective actuator of a plurality of actuators to drive the respective valve of a plurality of valves in a first direction upon determining that the respective monitoring parameter associated with the respective chamber is higher than the respective threshold. The respective valve may be connected to the respective secondary end or the respective primary end of the respective chamber. The respective valve may be configured to control a fluid velocity of the media flowing through the respective chamber. Additional details of the valves are described throughout this disclosure and are not repeated here.

At block 312, operations may include sending a second driving signal to the respective actuator to drive the respective valve in a second direction upon determining that the respective monitoring parameter associated with the respective chamber is lower than the respective threshold.

In implementations, the first direction and the second direction may be different/opposite to each other. For example, the first direction may be clockwise, while the second direction may be counterclockwise. As another example, the first direction may be counterclockwise, while the second direction may be clockwise.

In implementations, driving the valves in the first direction or the second direction may have different/opposite effects on the resistance to the media. For example, driving the valves in the first direction may increase the resistance to the media, while driving the valves in the second direction may decrease the resistance to the media. As another example, driving the valves in the first direction may decrease the resistance to the media, while driving the valves in the second direction may increase the resistance to the media.

For example, by driving the valves at the outlet of the chamber in the first direction or the second direction, the pressure at the inlet of the chamber may be manipulated by increasing/decreasing the resistance to the media flowing through the chamber while leaving the volumetric flow rate of the media the same.

Figure 3C:
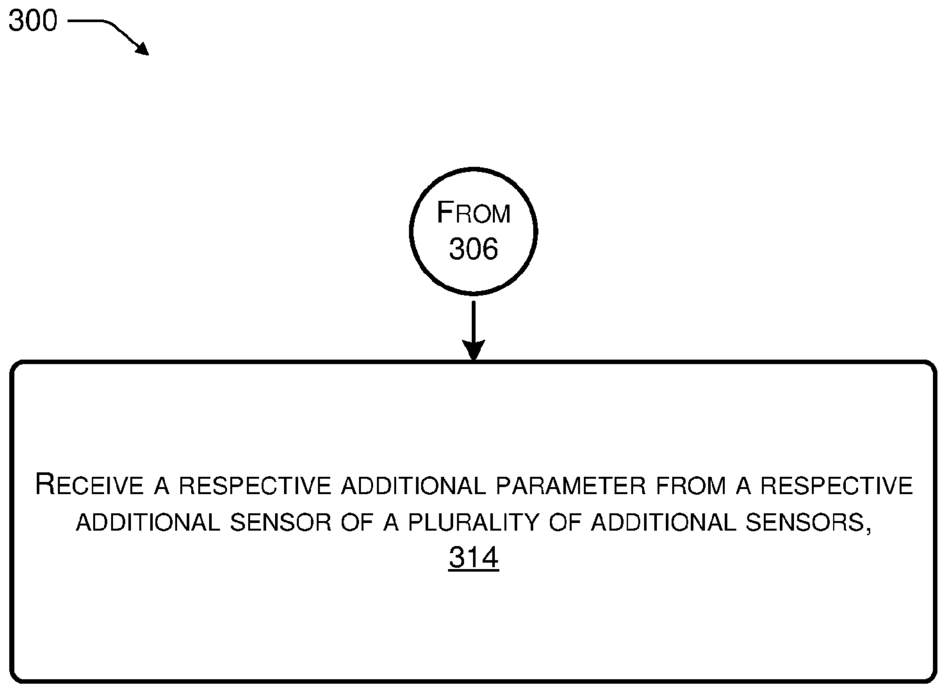

Referring to FIG. 3C, the process 300 may further include the following.

At block 314, operations may include receiving a respective additional parameter from a respective additional sensor of a plurality of additional sensors. In implementations, the respective additional sensor may be connected to the respective secondary end or the respective primary end of the respective chamber. The respective additional sensor may be configured to sense the respective additional parameter associated with the respective chamber.

In implementations, the additional parameter may be the pressure of the media flowing through the respective chamber, the flow rate of the media flowing through the respective chamber, etc. This disclosure is not limited thereto.

Additional details of the plurality of additional sensors and the additional parameter are described throughout this disclosure and are not repeated here.

Figure 3D:
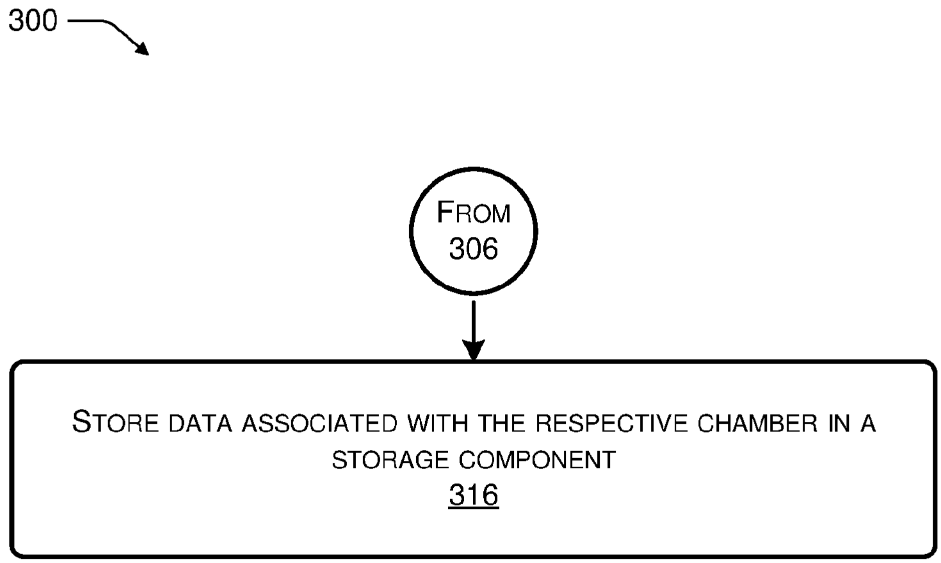

Referring to FIG. 3D, the process 300 may further include the following.

At block 316, operations may include storing data associated with the respective chamber in a storage component.

Figure 3E:
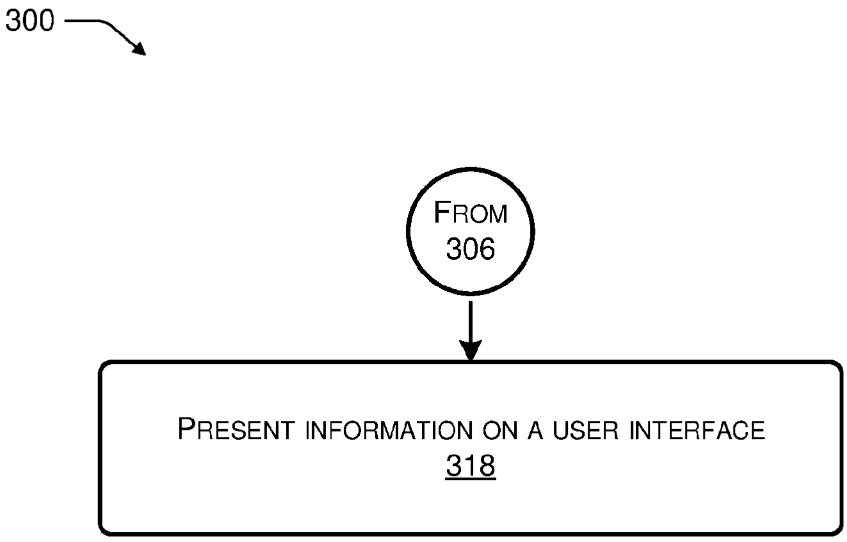

Referring to FIG. 3E, the process 300 may further include the following.

At block 318, operations may include presenting information on a user interface.

Figure 3F:
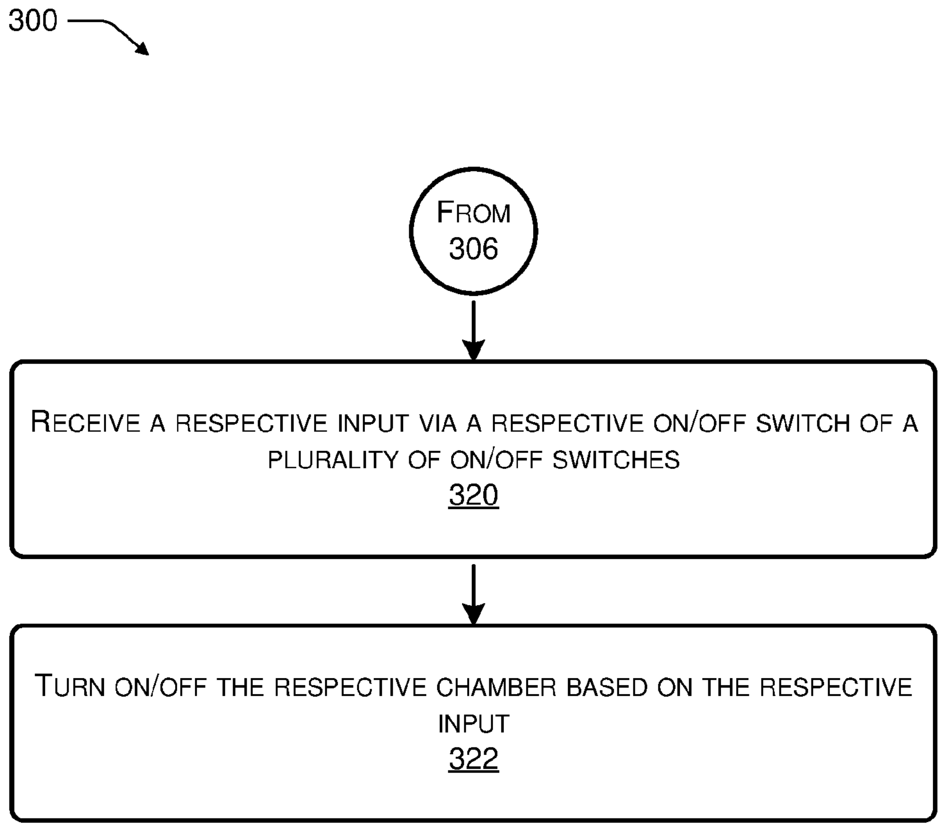

Referring to FIG. 3F, the process 300 may further include the following.

At block 320, operations may include receiving a respective input via a respective on/off switch of a plurality of on/off switches.

At block 322, operations may include turning on/off the respective chamber based on the respective input.

The process 300 may provide improvements to in vitro methods for modeling fluid flow. The improvements may include one or more of: controlling pump(s) and valves to manipulate one or more controllable parameters of the media flowing through the chamber; driving valves via actuators to control the media flowing through the chamber; manipulating the one or more controllable parameters of the media with a function of time; manipulating the pressure of the media by controlling the resistance of the media flowing through the chamber using valves (for instance, without employing headspace gases to increase or decrease pressure in the system); manipulating the flow rate and/or the pressure of the media in order to mimic multiple different flow rate waveforms and pressure waveforms over a period of time; running multiple chambers with different conditions in parallel; providing scalability/configurability of the system; and/or employing single-stage compliance chambers without air pockets.

Figure 4:
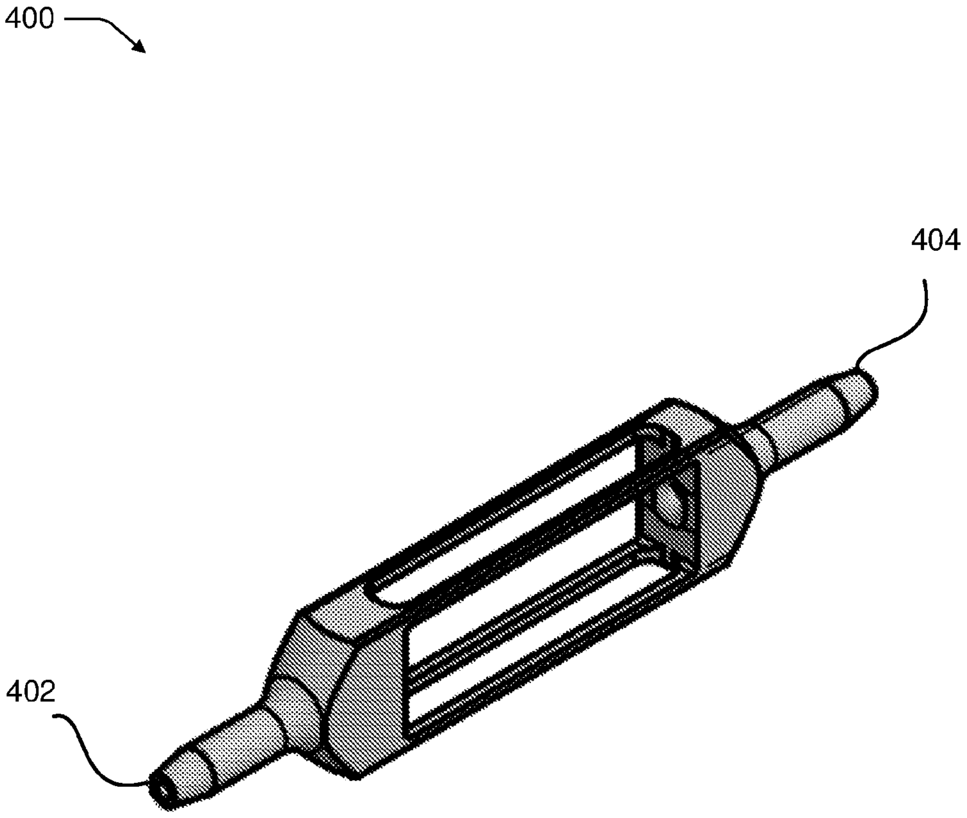
FIG. 4 illustrates an exemplary chamber according to implementations of this disclosure.

FIG. 4 illustrates an exemplary chamber 400 according to implementations of this disclosure. In implementations the chamber 400 may be used in systems and methods for modeling fluid flow according to implementations of this disclosure.

In implementations, the chamber 400 may have a primary end 402 and a secondary end 404.

In implementations, the chamber 400 may be imageable. For example, the chamber 400 may be a 360-degree imageable in situ chamber composed of a substantially transparent component base, such as a component comprising one or more of vinyl, nylon, or silicone. By way of further example, the following provides a list of material sheets that can be used and why they are considered useful or beneficial: Teflon (biocompatible, flexible, and has good structural integrity over time); Silicone (very biocompatible, flexible, readily available in multiple thicknesses, translucent, and can form watertight seals with many materials); PVC (relatively low cost, great for imaging the chambers); and Nylon (available in various thicknesses, very chemically stable, low cost, transparent, easy for imaging).

In implementations, the chamber 400 may be detachable from other parts of the system for modeling fluid flow and restorable into the system for modeling fluid flow. For example, the chamber 400 may be placed into a carrying case in which the chamber 400 may be detached from other parts of the system for modeling fluid flow and imaged. Furthermore, the chamber 400 may be restored back into the system for modeling fluid flow after imaged. In implementations, the carrying case may be produced by custom 3D printing, or any other suitable procedures. This disclosure is not limited thereto.

Even the chambers require samples/media to be fixed and then stained, by using the flexible/detachable chamber, the chamber is still intact and in a sterile environment for experiments to continue.

In implementations, the chambers may be produced as follows. For example, a clear flexible material sheet may be wrapped around custom made 3D printed endcaps. The clear flexible material may be transparent or translucent to allow at least partial transmission of light. The opening of the sheet may be then wrapped around itself and may be clamped by two metal rods. Inside the endcap may be a type of sealing material (such as urethane and the like) that acts as a seal for connectors (such as Luer locks and the like) between the chamber 400 and the tubing (not shown).

In implementations, the entire chamber together with the media inside may be placed into a custom 3D printed carrying case in which the chamber may be disconnected/detached from the other parts (such as the pump and the valves) of the system for modeling fluid flow and imaged. Moreover, the chamber 400 may be restorable back to the system, for instance, after being imaged.

Leakage from the chamber may affect the performance of the chamber. The chamber 400 may address the leakage issue by improving the seal.

In implementations, the chamber 400 may be made of clear material (such as vinyl and the like) that has tunable compliance. The clear material may be transparent or translucent to allow at least partial transmission of light. This would be advantageous compared to traditional microfluidic devices that are dependent on an external pump to control material compliance.

Persons with ordinary skills in the art may understand that though the shape of the chamber 400 shown in FIG. 4 is rectangular, the shape of the chamber 400 may be any suitable shapes such as cylindrical, spherical, funnel, irregular shape, or any shape that mimics the inner environment of human body such as organs, tissues, cells, and so on. This disclosure is not limited thereto.

Example 1

Bioreactors have become a critical step for the testing of new biomaterials and pharmaceuticals. Bioreactors need to be controllable, ideally high-throughput, and produce a biologically relevant environment. For example, in the brain, it is essential to recreate multiple flow-pressure profiles in a time-dependent manner and mimic brain fluid movement for a bioreactor to be more physiologic.

In Example 1, a scalable/configurable system for modeling fluid flow according to implementations of this disclosure (referred to as the FLO system hereinafter) is demonstrated that regulates flow rate, pressure, and pulsation amplitude. With the microcontroller technology described throughout this disclosure, multiple (for example, more than 12) chambers running in parallel are possible. The exemplified system for modeling fluid flow according to implementations of this disclosure may achieve the above goals by multiplexing a series of valves and pump(s) to control pressure and volumetric flow rate, instead of relying on head gas pressure. With the ability to control multiple parameters and the ease of use, both scientists and clinicians can use the system for modeling fluid flow according to implementations of this disclosure, for instance, to study the effects of pulsation amplitude of the fluid flow, flow rate, and pressure on intercellular interactions for both biomaterials and pharmaceuticals.

There is precedence for biomaterials behaving differently under varying shear stress and pressures. For instance, protein adsorption and cell attachment to biomaterials used for treating the neurologic disorder hydrocephalus are dependent on flow rate. Also, micromotion on this scale has been shown to influence cell migration to some chronically implanted neural probes. It is also known that the brain goes through cyclical periods of high and low mean flow rates, changes in bulk pressures, and pulsation amplitudes because of rudimentary processes such as circadian rhythm. Therefore, it is logical that these changes may impact neurological biomaterial performance in an as yet unknown way.

While there are multiple other variables that influence cell behavior, pressure, flow rate, and pulsation amplitude are among the easiest to manipulate. There are bioreactors devoted to controlling these factors, including LumeGen by Bangalore Integrated System Solutions ITE (BISS), the Supervising Unit for In vitro Testing (SUITE), and the bioreactor proposed by Mazzei et al. All these systems rely on peristaltic pump(s) to circulate media into chambers and a series of valves used to regulate gases going into the chamber. Some systems, like the one sold by BISS, can control up to six chambers in parallel, but this is the upper limit of most systems. These models are targeted toward only pharmaceuticals and not a combination of biomaterials and pharmaceuticals. The difference is the ability to embed the biomaterial into a physiologic environment.

Other model systems, such as microfluidic devices, focus on creating very high throughput environments in an easy-to-analyze size. However, this comes at the cost of size, which makes it difficult to study specific cellular responses to environmental changes and biomaterials. For instance, many microfluidic devices have difficulty in cooperating 3-dimensional substrates. While attempts have been made to change this shortcoming, particularly in brain-on-a-chip models, most substrate materials are added in such small quantities that they adhere to porous membrane structures instead of forming an independent structure. Additionally, because the substrates are separated by a membrane, cell communication is limited to cytokine transmission, not touch. This is detrimental to specific cell types (for instance, within the brain) that utilize contact for growth, such as astrocytes. These models also have limited operating times ranging up to 14 days.

In contrast, the system described herein (the FLO system) improves on the system by optionally controlling flow, pressure, and flow amplitude. Benefits may include running the chambers for more than a month, embedding the biomaterial into an extracellular matrix, and controlling multiple (for example, up to 15) chambers at once. Conversely, unlike traditional bioreactor systems that control pressure through the addition of gas, this Example 1 provides a system that controls pressure by changing the local speed of fluid moving through the pressure valve. This allows the possibility to change other factors, like chamber compliance. Additionally, with improved microcontroller technology, waveforms can be modified as a function of time and constantly monitored.

In this Example 1, the FLO may be programmed to mimic the pressures, flow rates, and pressure amplitudes seen in the brain. These values in the brain consist of 17 mmHg average pressure, 6-9 mmHg for pressure amplitudes, and 15-30 ml/hr flow rate. Such values may be chosen to mimic parameters that are significant in brain physiology and pathophysiology.

While the brain is used as the example model organ for the FLO system, any waveform can be programmed into the system. The FLO system is therefore applicable to virtually any organ system.

This Example 1 describes validation of three aspects of the FLO system: 1) that the readings obtained from the FLO system are similar to traditional techniques; 2) that the FLO system can manipulate flow rates while keeping pressures within a user defined range; and 3) that other parameters in the FLO system can be modified, such as mean wave amplitude.

Pressure

Figures 5A, 5B, 5C:
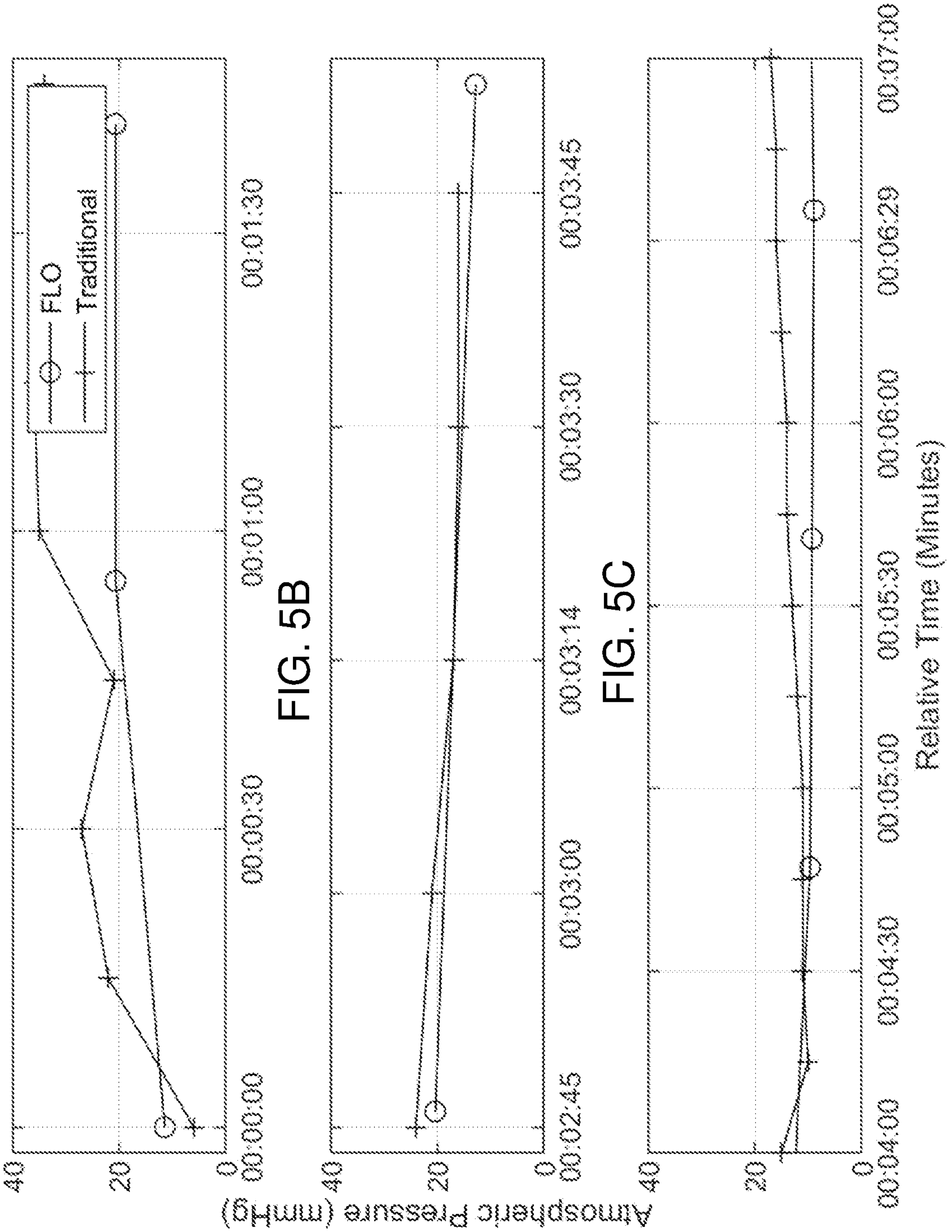
FIG. 5A, FIG. 5B, and FIG. 5C illustrate test results comparing the system for modeling fluid flow with the FLO according to implementations of this disclosure (referred to as the FLO system hereinafter) and a traditional system for modeling fluid flow without the FLO (referred to as the traditional system hereinafter) in terms of pressure over time.

FIG. 5A, FIG. 5B, and FIG. 5C illustrate test results comparing the system for modeling fluid flow with the FLO according to implementations of this disclosure (referred to as the FLO system hereinafter) and a traditional system for modeling fluid flow without the FLO (referred to as the traditional system hereinafter) in terms of pressure over time. For example, the FLO system may be the system 100 as described in this disclosure. For example, the traditional system may employ Codman Microsensors to sense the pressure.

In FIG. 5A, FIG. 5B, and FIG. 5C, horizontal axes represent relative time in minutes, while vertical axes represent atmospheric pressure in mmHg. In implementations, the bulk pressure detected by the FLO system is compared with the bulk pressure detected by the traditional system in terms of matching a threshold value defined by the user. For example, a target pressure/threshold of 17 mmHg may be used. The speed of the pump (in revolutions per minute) may be calculated based on flow rates of 30 ml/hr to 40 ml/hr. For example, in FIG. 5A, the flow rate may be 40 ml/hr; in FIG. 5B, the flow rate may be 30 ml/hr; and in FIG. 5C, the flow rate may be 40 ml/hr.

FIG. 5A, FIG. 5B, and FIG. 5C show no statistically significant difference between the FLO system and the traditional system.

Referring to FIG. 5A, when registering an over-pressure event, there is little delay (less than 1 minute) between registering the over-pressure event and the FLO system matching the target pressure/threshold.

Referring to FIG. 5B, when compensating for the over-pressure event, the FLO system has no delay from registering the decrease in pressure.

Referring to FIG. 5C, when the detected pressure is below the target pressure/threshold, the FLO system attempts to raise the pressure, there is a delay greater than two minutes between pressures rising in the chamber and the detected pressure is registered. While the FLO system attempts to match the target pressure/threshold of 17 mmHg, the target pressure/threshold is not reached consistently due to changing flow rates. This implies a longer equilibration time than initially predicted, because more pressure is needed in the air column to get a true positive.

Pressure Waveforms

Figure 6:
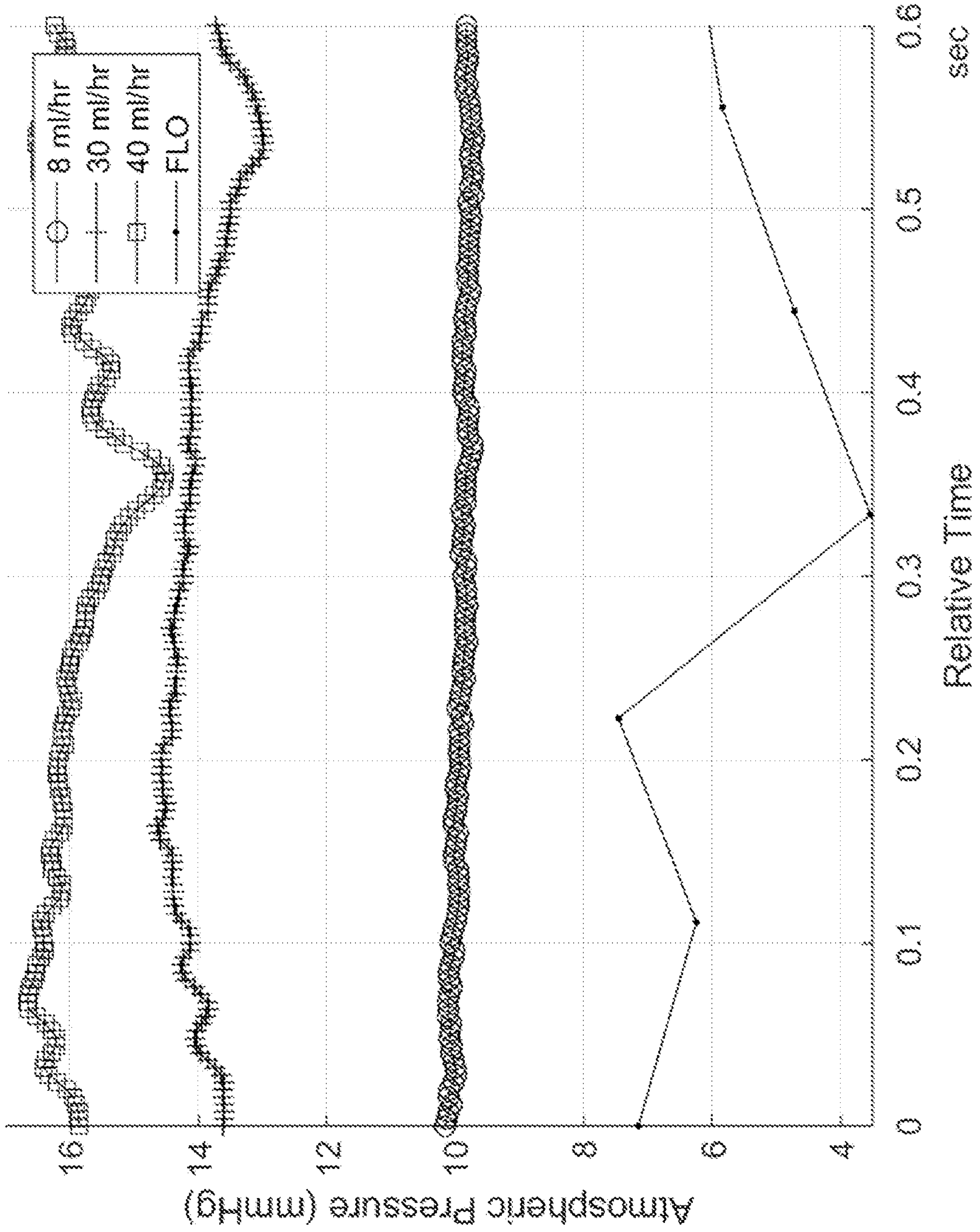
FIG. 6 illustrates test results comparing the FLO system and the traditional system in terms of pressure waveforms.

FIG. 6 illustrates test results comparing the FLO system and the traditional system in terms of pressure waveforms. In FIG. 6, the horizontal axis represents time in seconds, while the vertical axis represents atmospheric pressure in mmHg.

In order to verify that the pressure waveforms detected by the FLO system are the same as/similar to the pressure waveforms detected by the traditional system, three characteristics may be compared: mean frequency, mean amplitude, and Fast Fourier Transforms (FFTs). The FLO system may be set to a constant target pressure/threshold of 17 mmHg with a flow rate of 30 ml/hr. The traditional system may be set to a constant target pressure of 17 mmHg, with flow rates of 8 ml/hr, 30 ml/hr, and 40 ml/hr respectively. The frequencies and amplitudes of the pressure waveforms may be calculated.

FIG. 6 shows that while the waveforms of the traditional system with flow rates of 30 ml/hr and 40 ml/hr, and the waveform of the FLO system running at the flow rate of 30 ml/hr have the similar amplitudes and frequencies, the waveform of the traditional system with the flow rate of 8 ml/hr is different from other waveforms in terms of amplitudes and frequencies. Additional details are provided in Table 1.

TABLE 1

Pressure characteristics associated with chambers
Pressure Characteristics (with 0.38 mm bore tubing)

| Flow Rates | Traditional system 8 ml/hr | Traditional system 30 ml/hr | Traditional system 40 ml/hr | FLO system 30 ml/hr |
|---|---|---|---|---|
| Mean Frequency (mmHg) | 4.0410 | 5.3849 | 5.8147 | 5.0534 |
| Frequency Standard Deviation (mmHg) | 0.1709 | 0.1696 | 0.5896 | 2.5556 |
| Mean Amplitude (mmHg) | 0.0354 | 0.0620 | 0.0778 | 3.1646 |
| Amplitude Standard Deviation (mmHg) | 0.0015 | 0.0054 | 0.0127 | 2.0295 |

As shown in Table 1, there is no significant difference ($p>0.05$, where the p-value is the probability of obtaining results at least as extreme as the observed results of a statistical hypothesis test, assuming that the null hypothesis is correct) between the traditional system with the flow rates of 30 ml/hr and 40 ml/hr, and the FLO system in terms of the mean frequency, the frequency standard deviation, the mean amplitude, and the amplitude standard deviation. However, the traditional system with the flow rate of 8 ml/hr shows a significant difference.

Figure 7:
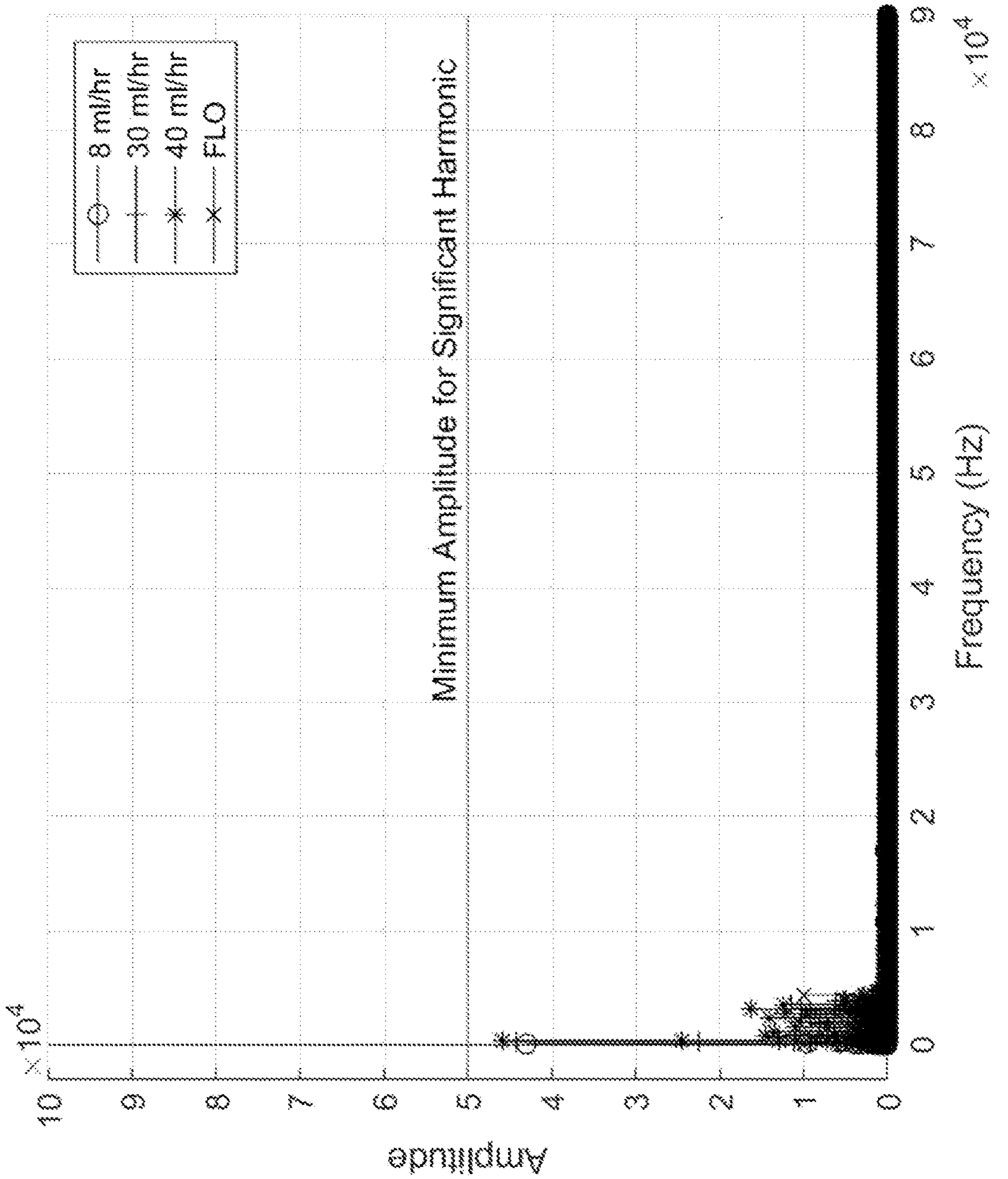
FIG. 7 illustrates test results comparing FLO system and the traditional system in terms of Fast Fourier transform (FFT) of characteristics associated with the chamber such as the change in compliance of a compliance chamber.

FIG. 7 illustrates test results comparing the FLO system and the traditional system in terms of FFT of characteristics associated with the chamber, such as a change in compliance of a compliance chamber. In FIG. 7, the horizontal axis represents frequency in Hertz, while the vertical axis represents the amplitude in mmHg.

The FFT converts a signal in the time domain into the frequency domain. The FFT works by decomposing an equation into an infinite series of sines and cosines to match the input waveform. The series can then be analyzed. In implementations, the FFT of characteristics associated with the chamber may be used to determine the amount of compliance inside the chamber or body part.

The pressure waveforms of the traditional system with the flow rates of 30 ml/hr and 40 ml/hr, and the FLO system shown in FIG. 6 may be converted into the FFT graph shown in FIG. 7.

Referring to FIG. 7, not only is there extensive overlap in the raw signals but the FFT graphs also show a fundamental frequency at 0 Hertz and no other harmonic frequencies. Harmonic frequencies may be defined as at least half of the fundamental frequency. Such results imply that no other significant distortion due to flexing of the chambers or peristaltic tubes.

Flow Rate Waveforms

Figure 8:
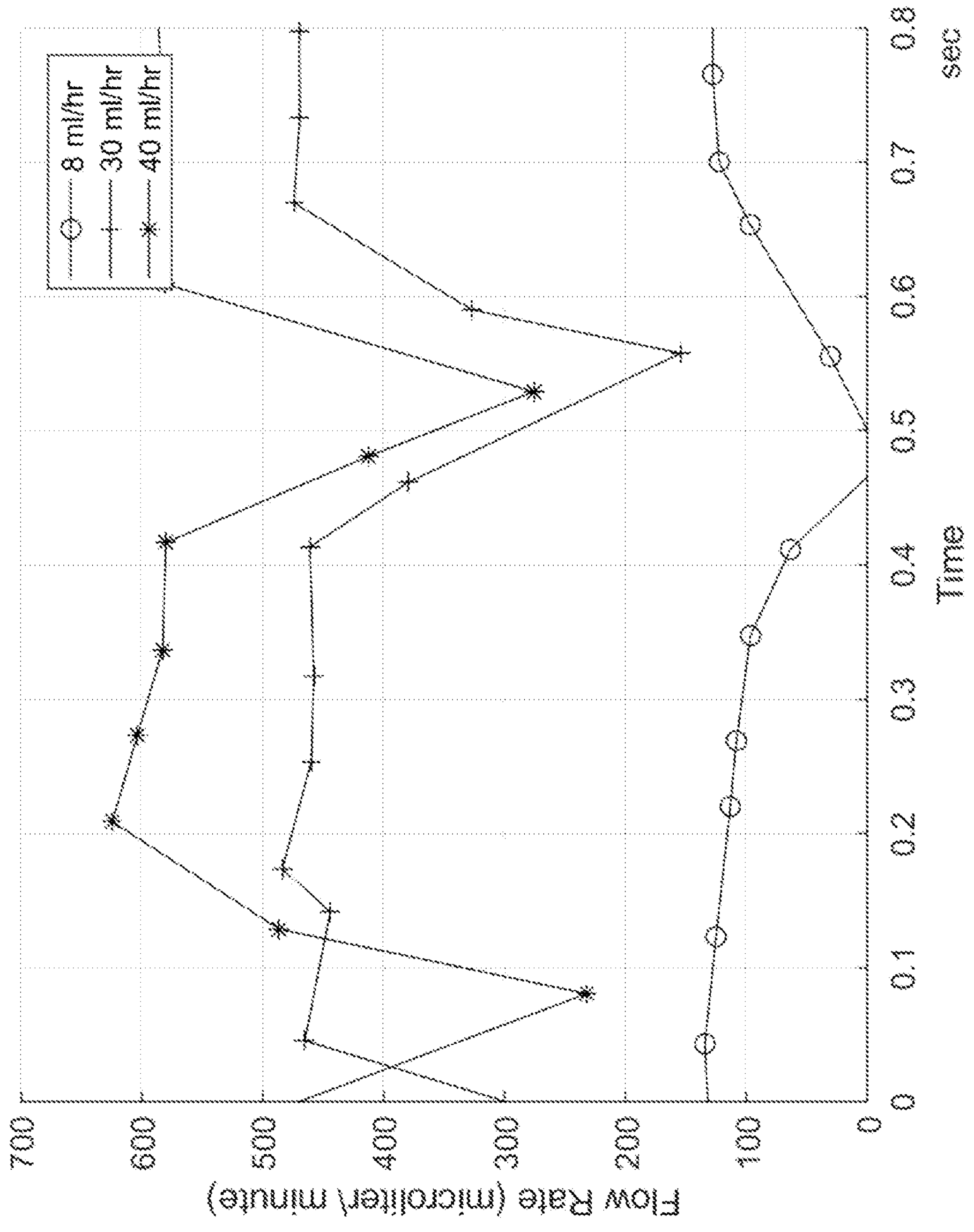
FIG. 8 illustrates flow rate waveforms of the traditional system.

FIG. 8 illustrates flow rate waveforms of the traditional system. In FIG. 8, the horizontal axis represents time in seconds, while the vertical axis represents flow rate in microliter/minute. For example, the traditional system may be set to the flow rates of 8 ml/hr, 30 ml/hr, and 40 ml/hr.

Referring to FIG. 8, statistics show a significantly different amplitude with regards to the 8 ml/hr setting ($p<0.05$), while no significant difference is shown in frequencies between the flow rates of 8 ml/hr, 30 ml/hr, and 40 ml/hr. Additional details are provided in Table 2. However, the 8 ml/hr theoretical set matched the actual flow rate. Finally, both the theoretical 30 ml/hr and 40 ml/hr sets did not show a significant difference between amplitude or frequency, as reflected by FIG. 8.

TABLE 2

Flow rate characteristics associated with chambers
Flow Rate Characteristics (with 0.38 mm bore Tubing)

| Flow Rates (ml/hr) | Traditional System 8 ml/hr | Traditional System 30 ml/hr | Traditional System 40 ml/hr | FLO System 30 ml/hr |
|---|---|---|---|---|
| Mean Frequency | 4.1726 | 4.4891 | 4.2464 | 3.5508667 |
| Frequency Standard Deviation | 1.0102 | 1.7143 | 1.3517 | 1.351 |
| Mean Amplitude | 21.2782 | 110.5130 | 145.4964 | 92.079967 |
| Amplitude Standard Deviation | 0.5165 | 2.2313 | 4.3042 | 6.4526 |
| Bulk Flow Rate | 7.2801 | 23.8946 | 30.8753 | 25.414767 |
| Bulk Flow Rate Standard Deviation | 1.7714 | 5.1722 | 5.1758 | 2.6629266 |

in Table 2, headings show predicted flow rates. There is no significant difference in frequencies ($p>0.05$), while there is a significant difference in amplitudes between 8 ml/hr and 30 ml/hr.

Figure 9:
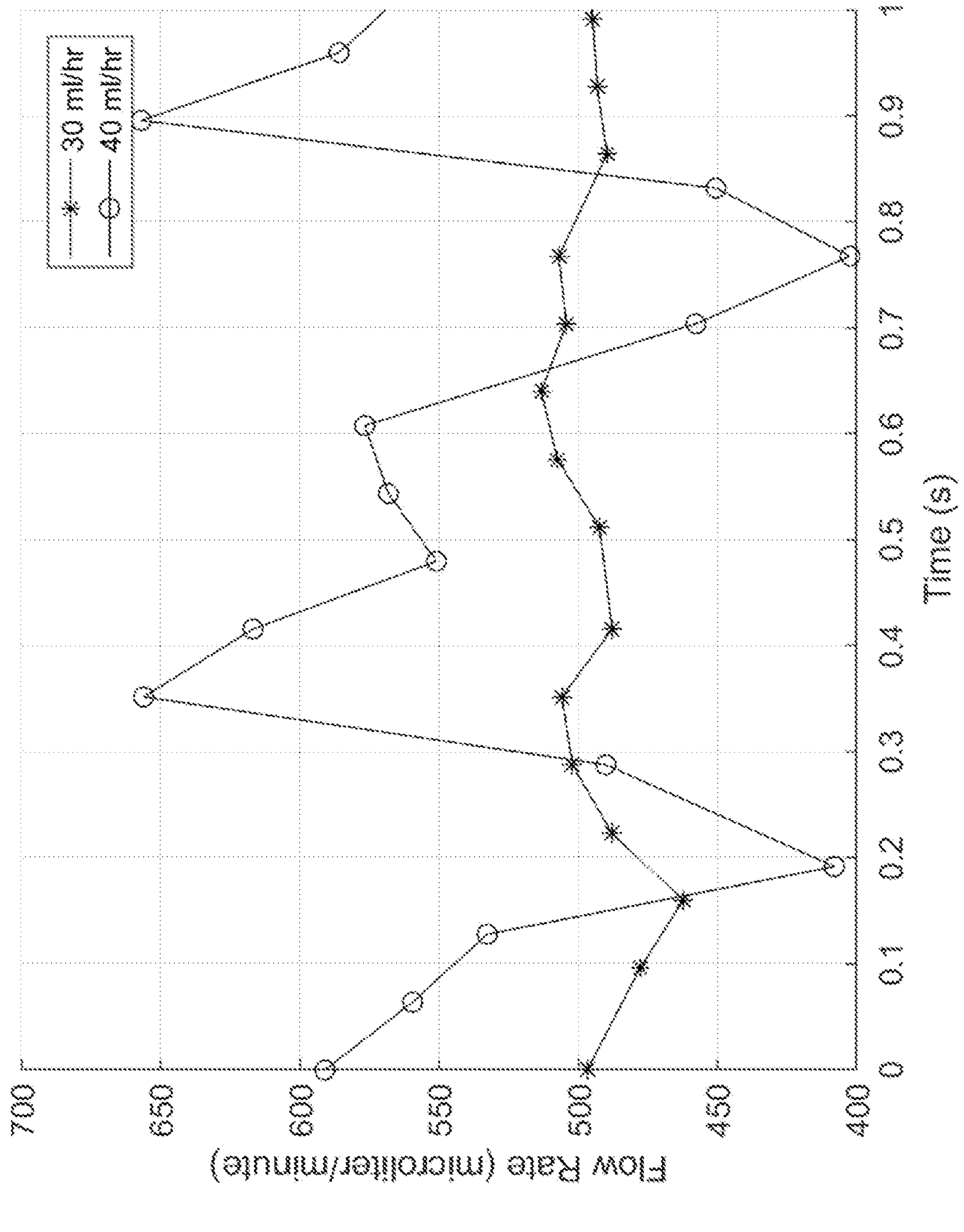
FIG. 9 illustrates flow rate waveforms of the FLO system with 0.38 mm bore tubing.

FIG. 9 illustrates flow rate waveforms of the FLO system with 0.38 mm bore tubing. In FIG. 9, the horizontal axis represents time in seconds, while the vertical axis represents flow rate in microliter/minute.

For example, to test the capabilities of the FLO system to maintain a target flow rate/threshold, the FLO system may be set to the flow rates of 30 ml/hr and 40 ml/hr. The flow rate waveforms of the FLO system are compared to the flow rate waveforms of the traditional system in which chambers are running at constant speeds of 25 rpm and 33 rpm, corresponding to flow rates of 30 ml/hr and 40 ml/hr respectively. The flow rate waveforms of the FLO system showed no statistically significant difference in amplitude, frequency, or flow rate ($p>0.05$). This is supported by graphs showing the flow rate over time indicating a period of about 0.4-0.6 seconds and amplitudes of about 25-150 microliters (FIG. 9) which are similar to the flow rate waveforms of the control 25 rpm and 33 rpm (FIG. 8). However, both target flow rates were similar to each other, indicating some differences present in the FLO system.

Figure 10:
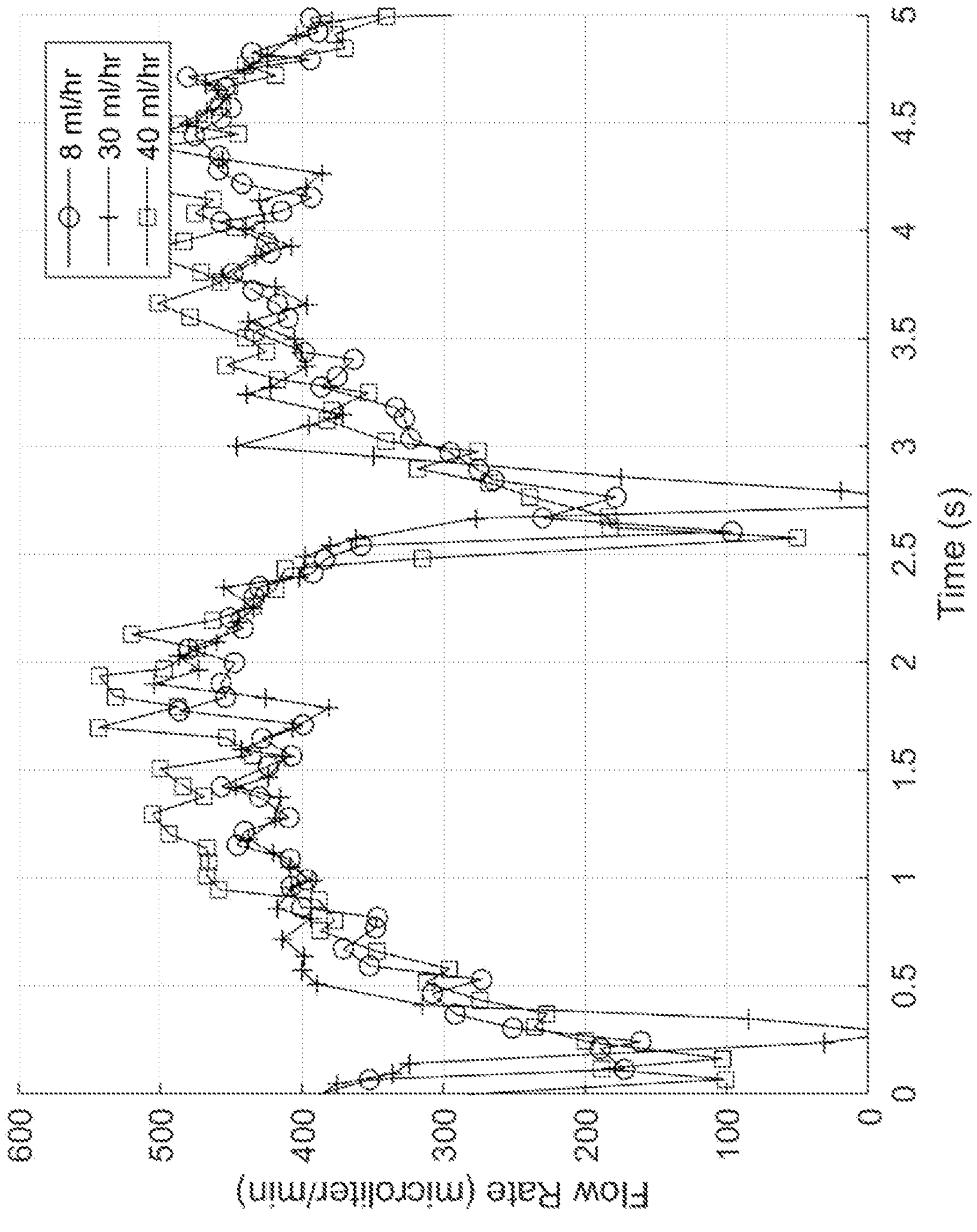
FIG. 10 illustrates flow rate waveforms of the FLO system with 1.02 mm bore tubing.

FIG. 10 illustrates flow rate waveforms of the FLO system with 1.02 mm bore tubing. In FIG. 10, the horizontal axis represents time in seconds, while the vertical axis represents flow rate in microliter/minute.

To manipulate pulsation amplitude while maintaining the shear stress, 1.02 mm bore tubing may be used in place of 0.38 mm bore tubing. Appropriate speed (in rpms) may be calculated to maintain flow rates based on the change in cross-sectional area between the 0.38 mm bore and 1.02 mm bore tubes. To verify the calculations, flow rates may be calculated in MATLAB and compared via a one-sample T-test. The one-sample t-test is a statistical hypothesis test used to determine whether an unknown population mean is different from a specific value.

Only the 40 ml/hr matched the predicted value. Additionally, when comparing the flow rate waveforms of three speeds to each other, the waveform of the flow rate 40 ml/hr is significantly different from the waveforms of other flow rates.

Finally, when comparing the amplitude and frequency, no significant difference is found between each of the 1.02 mm tubes, which can be seen in FIG. 10. Referring to FIG. 10, the functions/waveforms line up in their peaks, troughs, and frequencies. However, while the frequencies of the waveforms with 1.02 mm tubing stay similar to the frequencies of waveforms with 0.38 mm tubing, the amplitudes of the waveforms with 1.02 mm are nearly doubled compared to the amplitudes of the waveforms with 0.38 mm tubing for the flow rates of 8 ml/hr and 40 ml/hr. Additional details are provided in Table 3.

TABLE 3

Flow Rate Characteristics
Flow Rate Characteristics (with 1.02 mm Bore Tubing)

| Flow Rates (ml/hr) | 8 ml/hr | 30 ml/hr | 40 ml/hr |
|---|---|---|---|
| Mean Frequency | 3.2275 | 3.9122 | 4.2207 |
| Frequency Standard Deviation | 0.2676 | 0.3025 | 0.8002 |
| Mean Amplitude | 40.4464 | 81.8513 | 212.0940 |
| Amplitude Standard Deviation | 0.7581 | 1.3132 | 5.6750 |
| Bulk Flow Rate | 12.7253 | 24.8924 | 53.6856 |
| Bulk Flow Rate Standard Deviation | 0.228792 | 0.402876 | 0.97341 |

In Table 3, the flow rate is significantly higher than the predicted value for the 8 ml/hr and 40 ml/hr groups ($p<0.05$). Additionally, there is a significant increase in amplitude between the flow rate waveforms with 0.38 mm bore tubing and the 1.02 mm bore tubing.

Discussion

Most bioreactors are meant to test biomaterials in a semi-dynamic, short-term environment. The FLO system aims to address these gaps by improving the traditional system (for example, the system created by Harris et al.; US Patent Publication No. 2012/0060622), to allow multiple pressure and flow waves while creating an environment suitable for long-term biomaterials experiments.

The FLO system may manipulate the pressure by increasing the resistance on the outlet of the chamber using a variable valve, which is different from the traditional system that uses headspace gases to increase or decrease the pressure. The FLO system is instead based on the Bernoulli equation:

$$P_1 + \frac{1}{2}\rho V_1^2 + \rho g h_1 = P_2 + \frac{1}{2}\rho V_2^2 + \rho g h_2 \quad \text{Equation 1}$$

In Equation 1, subscript 1 indicates the variables inside the chamber; subscript 2 indicates energies occurring past the variable valve. P indicates pressure, ρ indicates density, z indicates height above table, V indicates velocity of fluid ($m\ s^{-1}$), g indicates gravitational constant. Equation 1 represents all forms of usable energy in a flowing system. Note that because there is no height change, as the pressure goes up, the velocity must decrease around the variable valve.

The experiments performed suggest that the FLO system follows the Bernoulli equation. For instance, FIGS. 5A-5C illustrate that the FLO system could get the chamber at a specific pressure at different flow rates. Even though the graphs do not show a straight line consistently at the target pressure of 17 mmHg, every time the flow rate changed, a spike in pressure is shown followed by a slow manipulation towards 17 mmHg (FIG. 5C). The initial spike came from the immediate change in volumetric flow (FIG. 5B) from the pump, while the slow changes came from the FLO system moving the resistance on the variable valve, for instance, by changing of the cross-sectional area separating the two tubes. This implies that another method of action is taking place when being filled as opposed to being discharged, such as a longer time to fill the air column. The graphs of FIGS. 5A-5C show that given enough time at a flow rate/pressure combination, the FLO system can meet the target pressure/threshold. For example, as shown in FIGS. 5A-5C, the time to meet the target pressure/threshold appears to be approximately 3 minutes.

FIG. 7 shows a single major peak at 0 hertz, which indicates no compliance of the chamber. This is because each line on an FFT indicates elastic deformation of the organ/bioreactor. The FFT deconstructs the signal into an infinite sum of sines and cosines to create a specific line graph of interferences creating the signal. This has become one of the gold standards for studying waveform activities. While other noises were seen on the graphs in FIG. 7, the noises can be explained by the insignificant elastic deformations of the tubing, air pockets, and subtle vibrations.

In FIG. 8 and FIG. 9, both the frequency and flow rate may look suspect because the pump speeds (in rpms) are set higher, for example, 25 rpm and 33 rpm, respectively. An increase in wave frequency would be expected, as each time the roller compresses the peristaltic tubing, that event may be recorded. The results leave little explanation for why flow rates are heavily correlated in the pre-experiment phase but not the experimental phase. A common issue that may have affected the study's outcome includes having small leaks in the chamber. This can be addressed by creating chambers with a better seal. Furthermore, confirming whether other flow rates, such as 12 ml/hr, including in the 1.02 mm bore tubing, would be advantageous, as this is another commonly used value to flow rates in the brain.

While the FLO system is exemplified herein to study biomaterials related to hydrocephalus, the FLO system can be adapted to study other materials and specific biologic responses. A potential scenario includes testing traumatic brain injury and white blood cell infiltration into the ventricular space. This is something that is already documented by animal studies. However, the effects of white blood cells on the immune-privileged brain are still largely unknown. It is known that white blood cells (such as neutrophils) can manipulate their shape based on pressures and flow rates to get through tight membranes. Additionally, blood cells usually do not enter the interstices of the brain unless there is traumatic brain injury (TBI). Moreover, the TBI would also activate macrophages to have M1 characteristics (polarizing states of macrophages), thereby potentially causing neurodegeneration through oxidative stress. Research into such situations in a controlled in vitro environment can help explain why outcomes with neural implants so often go wrong.

Because the FLO system is designed to be high-throughput, the FLO system can be used to study pharmaceuticals in a robust manner. Treatments are designed around carefully identified biological mechanisms. An example of this discrepancy is the bioavailability of nitric oxide. During strenuous activities, such as exercise, the bioavailability of nitric oxide has been shown to increase compared to homeostatic conditions. However, in longer term studies, organic nitrates have also been shown to produce nitrate tolerance. Both conditions are impossible to study with the traditional system, because the traditional system cannot create the acute environment of strenuous activities nor the everyday fluctuations known to happen.

The FLO system may be used to model other organ systems, such as the heart, kidneys, and liver. This could lead to integrating a series of organ systems similar to the ones seen in the SUITE model and in multi-organ on a chip model. Examples may include the placement of hydrogels into confined areas for unidirectional expansion, similar to myocardial systems, and the addition of a larger 3D cellular matrix which allows for closer cellular communication.

These types of studies would elucidate interdependency of other bodily signals on foreign body response to biomaterials.

Another envisioned embodiment is a version of the described system that is made of clear material such as vinyl that can have tunable compliance. The clear material may be transparent or translucent to allow at least partial transmission of light. This would be a step away from current technologies in microfluidic devices that are dependent on an external pump to control material compliance, instead focusing on a single complete system.

Additional cell stimuli, including various cytokines, can be added to the exemplified FLO system to mimic biomaterial insertion, cell-cell communication, and cell activation.

In implementations, the sensing range of the FLO system may be increased. The FLO system may be portable to image cells that attach in real time.

Conclusion

In this Example 1, the FLO system is described and can mimic multiple different flow rate waveforms and pressure waveforms, over a period of time, by manipulating the flow velocity of the medium. The FLO system opens the door to test new biomaterials' reactions and cellular mechanisms in real time, as well as responses to test compounds and test conditions. The FLO system proved scalable/configurable, running multiple chambers in parallel at once and capable of adding more chambers as needed. The FLO system allows for better optimization and statistical analysis to be carried out by researchers, clinicians, and corporations alike. Furthermore, the FLO system proved that different factors (such as amplitude of peaks) can be manipulated aside from flow and pressure. Improvements of the FLO system may include increasing the sensing range of the FLO system to better accommodate multiple organ systems like the brain, heart, and kidneys.

Experimental

The FLO system used for the described experiments may include a reservoir, chambers, biomaterial, and static valves. Cell culture media may be driven through 1.6 mm silicone tubing and emptied into the chamber. Inside the chamber, pieces of catheters (such as Medtronic ventricular catheters and the like) cut approximately 5 cm from the drainage eye may be embedded via a lock system (such as a Luer lock system and the like). The lock system may be attached to a valve (such as a High-Pressure Medtronic Flow Controlled valve and the like) via an additional 75 cm of silicone tubing. The fluid/media may be circled back to the reservoir. To drive fluid/media through the FLO system, a pump (such as a Watson Marlow 323 DU peristaltic pump equipped with a 314MC attachment) may be employed, using 0.38 mm bore or 1.02 mm bore peristaltic tubing. For controls, the system may run at 7, 25, and 33 revolutions per minute (rpms) for at least 2 minutes per test sample. The target flow rates/thresholds may include 8, 25, and 33 ml/hour and represent standard flow rates measured for humans over a 24 hours period.

Media Creation and Priming

Experiments may be conducted with cell culture media including 10% Fetal Bovine Serum (FBS) (ScienceCell, Carlsbad, CA, USA), 1% penicillin-streptomycin (Thermo Fisher Scientific, Waltham, MA, USA), and Dulbecco's Modified Eagle Medium (DMEM) (Thermo Fisher Scientific, Waltham, MA, USA). Such combination is used because the viscosity thereof is slightly higher than the viscosity of water, approximately 0.94 cP[25], and allows for protein adsorption onto the valve mechanism.

To prime the system, 70% ethanol may be first run through the chamber system for at least 20 minutes to decrease the bacterial load and dissolve any remaining particles. Cell culture media may be run through the FLO system for at least two hours to coat the chambers with proteins and remove any ethanol residue. The media may be replaced before the start of any tests. The wash and reset process may be completed every seven days.

Pressure Waveform Testing

To obtain the average pressure over time, a Codman® Microsensor® attached to a Codman® ICP Express® monitor may be placed adjacent to the chamber via a 3-way Luer lock and 10 cm fluid column. The Microsensor® may be calibrated according to the manufacturer's instructions between each chamber. Pressures, in mmHg, may be recorded every 15 seconds for 3 minutes per target flow rate/threshold.

To obtain the pressure data including amplitude, frequency, and waveform shapes, a SP200 Pressure Control Unit (Transonic, USA) may be connected to a 1.6 French rodent catheter. The catheter may be calibrated, hydrated, and zeroed between each chamber per the manufacturer's instructions. Like the Codman® insertion technique, the Microsensor® may be placed adjacent to the fluid via a 3-way Luer lock and 10 cm fluid column. A Tuohy Borst valve (Qosina, USA) may be used to close the system and care may be taken to not damage the sensor shaft. Pressures in mmHg may be continuously recorded and read using the LabScribe data package. Each chamber could run for 3 minutes per theoretical flow rate.

Flow Waveform Testing

To calculate the flow rate and flow patterns coming out of the chamber, a scalable Link Interface (SLI) liquid flow sensor (Sensiron, Switzerland) may be placed in series with the catheter directly outside the chamber. It may be primed with 1% w/v Tergezyme® detergent and water, deionized water, and 90% v/v isopropanol alcohol. The SLI sensor may be programmed to use 16-bit resolution linearized data sampling. When connecting to the sensor, care may be taken to eliminate any air pockets in the chamber. During each FLO system test, theoretical flowrates of 8, 30, and 40 ml/per hour may be used, which extrapolated to 7, 25, and 33 RPMs. Outputs may be read and recorded using the stock Sensirion RS485 program, and may be saved as microliters/minute.

FLO Design

The FLO (as exemplified in the current Example 1) may be controlled by an Arduino 2560 and may have three distinct functions: sensing the data, manipulating the parameters in the chamber system, and recording the results. This is done through two custom printed circuit boards (PCBs) (JLCPCB, Hong Kong, CN), one with which the user interfaces and another devoted to interfacing with the chambers. To accomplish the tasks, the FLO may use a combination of serial peripheral interface (SPI), inter-intercommunication (12C), Serial-in/Parallel-out (SIPO), and Universal Asynchronous Receiver/Transmitter communication systems (UART).

To sense the pressure, the FLO system may use 74 cm air columns connected to 3-way Luer locks in line with the fluid flow (FIG. 1A and FIG. 1B). The air columns may be connected to HSCNARNN015PAAA5 absolute pressure sensors (Mouser, USA). To transform the absolute pressure readings into atmospheric pressure, a constant 100 kPa may be subtracted from the FLO values. The pressure sensor may send analog signals to a 10-bit analog-to-digital-converter (ADO) (MCP3008, Digikey Electronics, USA). The ADO may connect to a 4.5 voltage reference (Digikey Electronics, USA). The ADC may relay the information to the Arduino via the SPI bus at 3.6 MHz using the Adafruit MCP3008 library.

To control the peristaltic pump, the stock RS232 communication bus on the pump may be used. A UART-to-R3232 adapter may transform the RS232 voltage level into appropriate transistor-transistor logic (Sparkfun, Noiwat, CO, USA). A linear relationship between revolutions per minute (RPM) and flow rate may be established, with the (138 mm bore peristaltic tubing being 0.0203 ml/min/RPM and showing a high correlation coefficient, $R^2>0.94$. The $R^2$ coefficient of determination is a statistical measure of how well the regression predictions approximate the real data points.

To control the pressure, the FLO may take an average of ten pressure readings from each chamber and use a threshold function to turn a Nema 17 stepper motor (STEPPERONLINE, USA) connected to the variable valve (Amazon, Seattle, WA, USA) (FIG. 2). The valve may increase or decrease the resistance to fluid flow, thereby changing the inline pressure while leaving the volumetric flow rate the same. To drive the stepper motors, each coil was connected to half of a TB6612 dual H-bridge (Digikey LLC, USA). The logic patterns of when to energize each coil may be pre-programmed into the Arduino. Each sequence, once selected by the threshold function, would be sent in binary to the SN54HC595 (Digikey Electronics, USA) serial in parallel out (SIPO) shift registers. The SIPO shift registers in turn may signal the TB6612 H bridges accordingly.

The ten data points used to find the average pressure may be sent to two different SD readers, to create the pressure waveform. As a further back-up, the FLO may have a total of four SD readers which ensures that if one pair of SD readers reach capacity or is disconnected, data can still be recovered. To choose which card reader is used, the FLO may go through a series of If-Else statements to determine if the cards are at capacity or not inserted properly. If either condition is broken for all SD cards, the user is alerted via the user interface. To interface with so many cards, FLO may use the open source SdFs library, which also allows the SD cards to be formatted using any of the File Allocation Table systems, including exFAT.

The user interface may include a combination of Organic Light Emitting Diode (OLED) displays (MiniArduino store, CN) and dual in-line package (DIP) switches (Digikey LLC, USA). The DIP switches form an electrical connection in series with a shift register to determine if there is power connected to the chamber. The OLED display not only shows values of each of the chambers but also warning signals, such as if the SD cards are no longer connected or if a chamber is inactive. To keep the FLO referenced to time, all actions are tied to a DS3231 real time clock module that records when any new data is recorded.

Power regulation may be achieved through a 12-volt alternating current-to-direct current wall adapter, which was then subdivided into 5- and 10-volt pathways using LM10841T-5.0 and LM7810 linear regulators respectively (Digikey Electronics, USA). These voltages may be galvanically isolated from each other and smoothed out via various aluminum and ceramic capacitors sizes. Applicable sizes may be chosen to optimize power distribution at each data transmission frequency (Digikey Electronics, USA). To make the physical connections, ground plane and power planes were employed. Such design not only distributes heat efficiently but also decouples analog signals.

Statistics

Three separate chambers may run in the FLO system and five chambers may run in the traditional system. Within each chamber, at least five observations may be made with the FLO model and more than 5000 with the traditional sensors. The samples were assumed non-parametric due to the small sample size. To analyze bulk pressure readings, area under the curves may be compared via a paired T-test. This was because of the varying times at which observations were taken from each chamber. Additionally, area outside the sensing range of the absolute pressure sensors were excluded from analysis. To compare pressure waveforms, parameters such as amplitude, frequency, and Fast Fourier Transforms (FFTs) may be compared. Computations and graphs may be made in MATLAB. Flow rates may be calculated by averaging the flow rate determined by the SLI liquid flow sensor. These may be compared to their theoretical values of 8 ml/hr, 30 ml/hr, and 40 ml/hr using a one-sample T-test. Furthermore, amplitude and frequency were compared between flow rates using a Kruskal-Wallis Test and Mann-Whitney post hoc. All statistical analysis was conducted in Statistical Package for the Social Sciences (SPSS) with an alpha of 0.05.

Representative Computer Architecture

Figure 11:
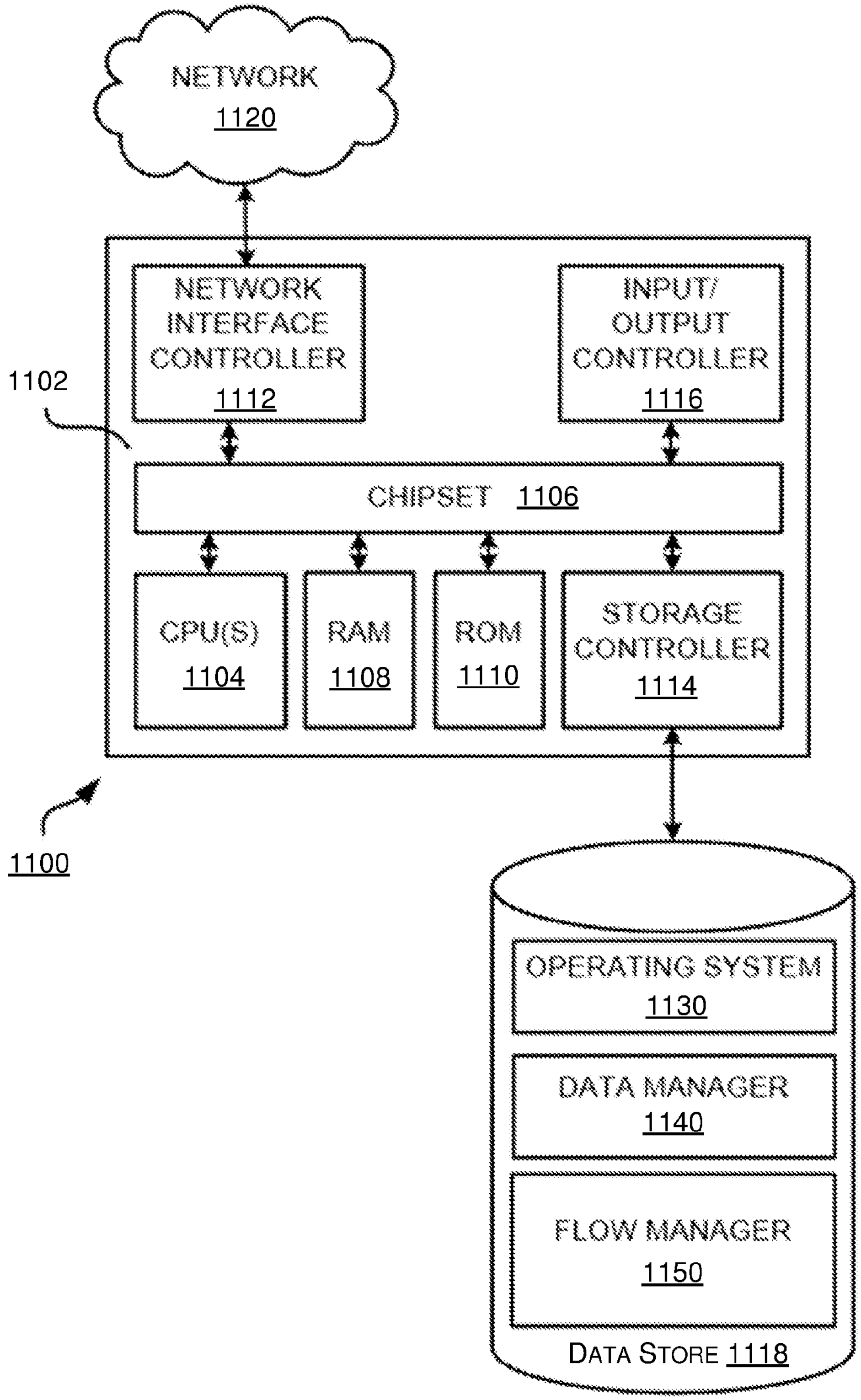
FIG. 11 illustrates an example computer architecture for a computer capable of executing program components for controlling fluid flow in a bioreactor, and/or monitoring and/or measuring one or more characteristics of fluid flow in a bioreactor, in a manner described herein.

FIG. 11 illustrates an example computer architecture for a computer 1100 capable of executing program components for controlling fluid flow in a bioreactor, and/or monitoring and/or measuring one or more characteristics of fluid flow in a bioreactor, in a manner described herein. The computer architecture shown in FIG. 11 illustrates a conventional server computer, workstation, desktop computer, laptop, tablet, network appliance, digital cellular phone, smart watch, or other computing device, and may be utilized to execute any of the software components presented herein. For example, the computer architecture shown in FIG. 11 may be utilized to execute software components for performing operations as described herein. The computer architecture shown in FIG. 11 might also be utilized to implement a computing device, or any other of the computing systems described herein.

The computer 1100 includes a baseboard 1102, or "motherboard," which is a printed circuit board to which a multitude of components or devices may be connected by way of a system bus or other electrical communication paths. In one illustrative example, one or more central processing units ("CPUs") 1104 operate in conjunction with a chipset 1106. The CPUs 1104 may be standard programmable processors that perform arithmetic and logical operations necessary for the operation of the computer 1100.

The CPUs 1104 perform operations by transitioning from one discrete, physical state to the next through the manipulation of switching elements that differentiate between and change these states. Switching elements may generally include electronic circuits that maintain one of two binary states, such as flip-flops and electronic circuits that provide an output state based on the logical combination of the states of one or more other switching elements, such as logic gates. These basic switching elements may be combined to create more complex logic circuits, including registers, adders-subtractors, arithmetic logic units, floating-point units and the like.

The chipset 1106 provides an interface between the CPUs 1104 and the remainder of the components and devices on the baseboard 1102. The chipset 1106 may provide an interface to a RAM 1108, used as the main memory in the computer 1100. The chipset 1106 may further provide an interface to a computer-readable storage medium such as a read-only memory ("ROM") 1110 or non-volatile RAM ("NVRAM") for storing basic routines that help to startup the computer 1100 and to transfer information between the various components and devices. The ROM 1110 or NVRAM may also store other software components necessary for the operation of the computer 1100 in accordance with the description herein.

The computer 1100 may operate in a networked environment using logical connections to remote computing devices and computer systems through a network, such as the network 1120. The chipset 1106 may include functionality for providing network connectivity through a network interface controller ("NIC") 1112, such as a mobile cellular network adapter, WiFi network adapter or gigabit Ethernet adapter. The NIC 1112 is capable of connecting the computer 1100 to other computing devices over the network 1120. It should be appreciated that multiple NICs 1112 may be present in the computer 1100, connecting the computer to other types of networks and remote computer systems.

The computer 1100 may be connected to a mass storage device 1118 that provides non-volatile storage for the computer. The mass storage device 1118 may store system programs, application programs, other program modules and data, which have been described in greater detail herein. The mass storage device 1118 may be connected to the computer 1100 through a storage controller 1114 connected to the chipset 1106. The mass storage device 1118 may consist of one or more physical storage units.

The computer 1100 may store data on the mass storage device 1118 by transforming the physical state of the physical storage units to reflect the information being stored. The specific transformation of physical state may depend on various factors, in different implementations of this description. Examples of such factors may include, but are not limited to, the technology used to implement the physical storage units, whether the mass storage device 1118 is characterized as primary or secondary storage and the like.

For example, the computer 1100 may store information to the mass storage device 1118 by issuing instructions through the storage controller 1114 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 1100 may further read information from the mass storage device 1118 by detecting the physical states or characteristics of one or more particular locations within the physical storage units.

In addition to the mass storage device 1118 described above, the computer 1100 may have access to other computer-readable storage media to store and retrieve information, such as program modules, data structures, or other data. It will be appreciated by those skilled in the art that computer-readable storage media is any available media that provides for the non-transitory storage of data and that may be accessed by the computer 1100.

By way of example, and not limitation, computer-readable storage media may include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

The mass storage device 1118 may store an operating system 1130 utilized to control the operation of the computer 1100. According to one example, the operating system comprises the LINUX operating system. According to another example, the operating system comprises the WINDOWS® SERVER operating system from MICROSOFT Corporation. According to another example, the operating system comprises the iOS operating system from Apple. According to another example, the operating system comprises the Android operating system from Google or its ecosystem partners. According to further examples, the operating system may comprise the UNIX operating system. It should be appreciated that other operating systems may also be utilized. The mass storage device 1118 may store other system or application programs and data utilized by the computer 1100, such as components that include the data manager 1140, the flow manager 1150 and/or any of the other software components and data described herein. The mass storage device 1118 might also store other programs and data not specifically identified herein.

In one example, the mass storage device 1118 or other computer-readable storage media is encoded with computer-executable instructions that, when loaded into the computer 1100, create a special-purpose computer capable of implementing one or more of the embodiments or examples described herein. These computer-executable instructions transform the computer 1100 by specifying how the CPUs 1104 transition between states, as described above. According to one example, the computer 1100 has access to computer-readable storage media storing computer-executable instructions which, when executed by the computer 1100, perform one or more of the various processes described herein. The computer 1100 might also include computer-readable storage media for performing any of the other computer-implemented operations described herein.

The computer 1100 may also include one or more input/output controllers 1116 for receiving and processing input from a number of input devices, such as a keyboard, a mouse, a touchpad, a touch screen, an electronic stylus, or other type of input device. Similarly, the input/output controller 1116 may provide output to a display, such as a computer monitor, a flat-panel display, a digital projector, a printer, a plotter, or other type of output device. It will be appreciated that the computer 1100 may not include all of the components shown in FIG. 11, may include other components that are not explicitly shown in FIG. 11, or may utilize an architecture completely different than that shown in FIG. 11.

Apparatus

Figure 12:
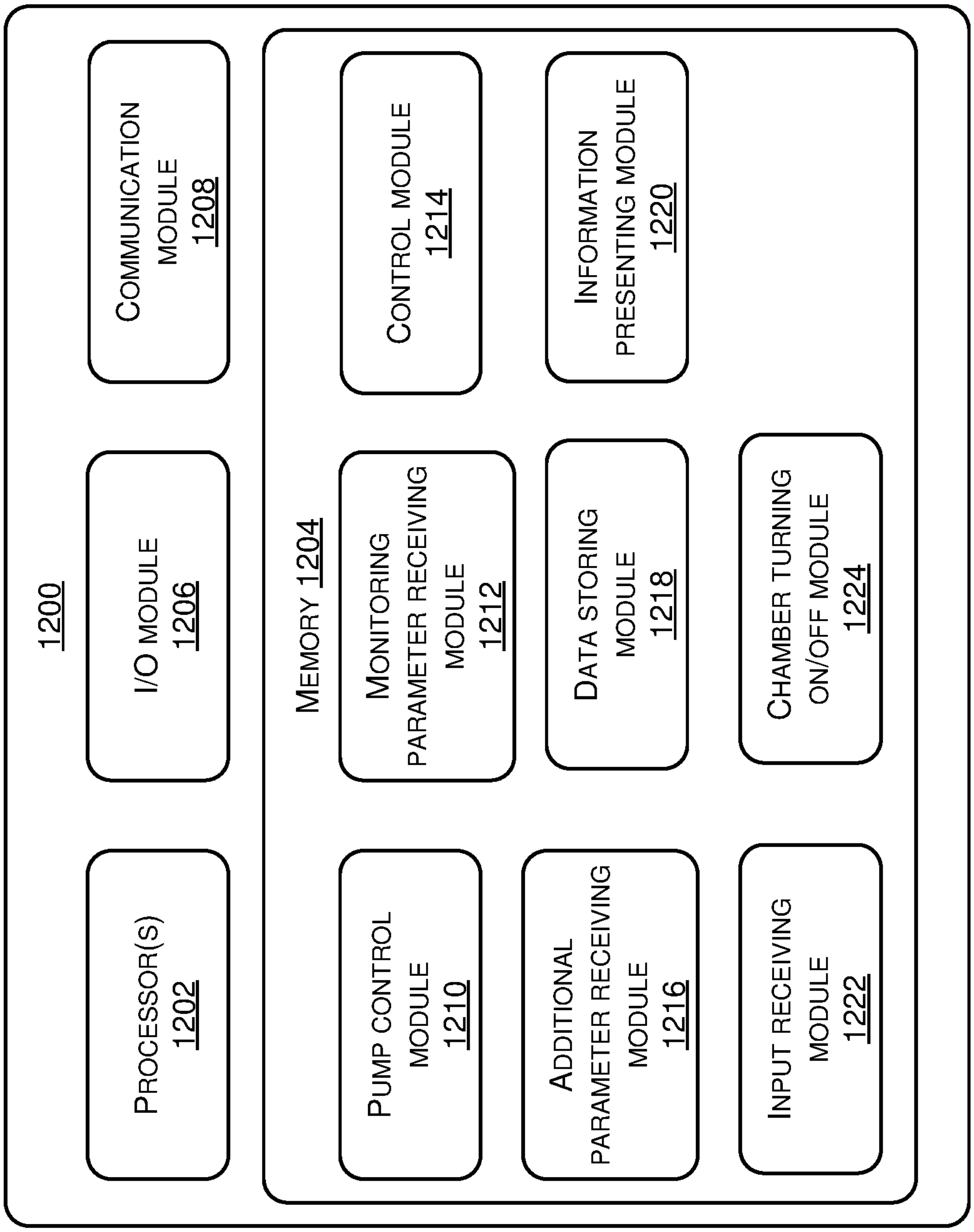
FIG. 12 illustrates an example apparatus for implementing the processes and methods described herein.

FIG. 12 illustrates an example apparatus 1200 for implementing the processes and methods described herein.

The techniques and mechanisms described herein may be implemented by multiple instances of the apparatus 1200 as well as by any other computing device, system, and/or environment. The apparatus 1200 shown in FIG. 12 is only one example of an apparatus and is not intended to suggest any limitation as to the scope of use or functionality of any computing device utilized to perform the processes and/or procedures described above. Other well-known computing devices, systems, environments and/or configurations that may be suitable for use with the embodiments include, but are not limited to, personal computers, server computers, hand-held or laptop devices, multiprocessor systems, microprocessor-based systems, set top boxes, game consoles, programmable consumer electronics, network PCs, minicomputers, mainframe computers, distributed computing environments that include any of the above systems or devices, implementations using field programmable gate arrays ("FPGAs") and application specific integrated circuits ("ASICs"), and/or the like.

The apparatus 1200 may include one or more processors 1202 and system memory 1204 communicatively coupled to the processor(s) 1202. The processor(s) 1202 may execute one or more modules and/or processes to cause the processor(s) 1202 to perform a variety of functions. In some embodiments, the processor(s) 1202 may include a central processing unit (CPU), a graphics processing unit (GPU), both CPU and GPU, or other processing units or components known in the art. Additionally, each of the processor(s) 1202 may possess its own local memory, which also may store program modules, program data, and/or one or more operating systems.

Depending on the exact configuration and type of the apparatus 1200, the memory 1204 may be volatile, such as RAM, non-volatile, such as ROM, flash memory, miniature hard drive, memory card, and the like, or some combination thereof. The memory 1204 may include one or more computer-executable modules (modules) that are executable by the processor(s) 1202.

The apparatus 1200 may additionally include an input/output (I/O) interface 1206 for receiving data to be processed, and for outputting the processed data. The apparatus 1200 may also include a communication module 1208 allowing the apparatus 1200 to communicate with other devices (not shown) over a network (not shown). The network may include the Internet, wired media such as a wired network or direct-wired connections, and wireless media such as acoustic, radio frequency (RF), infrared, and other wireless media.

The one or more computer-executable modules (modules) may include the following.

A pump control module 1210 may be configured to send a pump signal to a pump to set a status of the pump. In implementations, the pump may be connected to a respective primary end of a respective chamber of a plurality of chambers, for example, via tubing. The pump may be configured to move media to or from the respective chamber. Additional details of the pump are provided throughout this disclosure and are not repeated here.

A monitoring parameter receiving module 1212 may be configured to receive a respective monitoring parameter associated with the respective chamber from a respective sensor of a plurality of sensors. In implementations, the respective sensor may be connected to a respective primary end or a respective secondary end of the respective chamber. The respective sensor may be configured to sense the respective monitoring parameter associated with the respective chamber. Additional details of the sensors and chambers are provided throughout this disclosure and are not repeated here.

A control module 1214 may be configured to independently control the respective chamber by manipulating one or more controllable parameters associated with the respective chamber based on the respective monitoring parameter associated with the respective chamber.

The control module 1214 may be further configured to determine whether the respective monitoring parameter associated with the respective chamber is higher than a respective threshold; send a first driving signal to a respective actuator of a plurality of actuators to drive a respective valve of a plurality of valves in a first direction upon determining that the respective monitoring parameter associated with the respective chamber is higher than the respective threshold; and/or send a second driving signal to the respective actuator to drive the respective valve in a second direction upon determining that the respective monitoring parameter associated with the respective chamber is lower than the respective threshold. The respective valve may be connected to the respective secondary end or the respective primary end of the respective chamber. The respective valve may be configured to control a fluid velocity of the media flowing through the respective chamber. The second direction may be different/opposite to the first direction. Additional details of the valves are provided throughout this disclosure and are not repeated here. The respective threshold may a function of time. Additional details of the threshold are provided throughout this disclosure and are not repeated here.

An additional parameter receiving module 1216 may be configured to receive a respective additional parameter from a respective additional sensor of a plurality of additional sensors. In implementations, the respective additional sensor may be connected to the respective secondary end or the respective primary end of the respective chamber. The respective additional sensor may be configured to sense the respective additional parameter associated with the respective chamber.

A data storing module 1218 may be configured to store data associated with the respective chamber in a storage component. Additional details of the storage component are provided throughout this disclosure and are not repeated here.

An information presenting module 1220 may be configured to present information on a user interface. For example, the user interface may present instructions allowing the user to set the flow rate/speed of pump, the number of the chambers, turn on/off a respective chamber, etc. The user interface may present data/graphs associated with the respective chamber. The user interface may present warning signals, such as when the storage components are no longer connected or when a chamber is inactive. Additional details of the user interface are provided throughout this disclosure and are not repeated here.

An input receiving module 1222 may be configured to receive a respective input via a respective on/off switch of a plurality of on/off switches.

A chamber turning on/off module 1224 may be configured to turn on/off the respective chamber based on the respective input. Additional details of the on/off switch are provided throughout this disclosure and are not repeated here.

The apparatus 1200 may provide improvements to in vitro systems for modeling fluid flow. The improvements may include one or more of: controlling pump(s) and valves to manipulate one or more controllable parameters of the media flowing through the chamber; driving valves via actuators to control the media flowing through the chamber; manipulating the one or more controllable parameters of the media with a function of time; manipulating the pressure of the media by controlling the resistance of the media flowing through the chamber using valves (for instance, without employing headspace gases to increase or decrease pressure in the system); manipulating the flow rate and/or the pressure of the media in order to mimic multiple different flow rate waveforms and pressure waveforms over a period of time; running multiple chambers with different conditions in parallel; providing scalability/configurability of the system; and/or employing single-stage compliance chambers without air pockets.

Further, the processes discussed herein may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skills in the art will readily recognize that certain steps or operations illustrated in the figures above may be eliminated, combined, or performed in an alternate order. Any steps or operations may be performed serially or in parallel (unless context requires one or the other). Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skills in the art.

Additionally, those having ordinary skills in the art readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

Those of ordinary skill in the art will recognize in light of the present disclosure that many changes can be made to the specific embodiments disclosed herein and still obtain a like or similar result without departing from the spirit and scope of the disclosure.

Example Clauses

Clause 1. An improvement to an in vitro flow system that includes: a medical implant having an inner surface defining a bore, the bore having an inlet and an outlet; a fluid reservoir defining an inner chamber, the inner chamber configured to contain a desired fluid having at least one component, wherein the inner chamber of the fluid reservoir is in fluid communication with the outlet of the bore of the medical implant; a pump in fluid communication with the inner chamber of the fluid reservoir and the inlet of the bore of the medical implant, wherein the pump is configured to direct flow of the desired fluid to the inlet of the bore of the medical implant at a desired rate such that at least a portion of the inner surface of the medical implant contacts the desired fluid; and a first pressure valve positioned therebetween and in fluid communication with the outlet of the bore of the medical implant and the inner chamber of the fluid reservoir, wherein the first pressure valve is configured to modulate the flow of the desired fluid between the outlet of the bore of the medical implant and the inner chamber of the fluid reservoir, wherein the at least one component of the desired fluid includes at least one of nutrients, cells, proteins, and/or tissue; the improvement including a plurality of valves and pumps which control pressure and volumetric flow rate of the fluid.

Clause 2. An improvement to an in vitro flow system, the improvement including means to manipulate flow rate and pressure of the fluid as a function of time.

Clause 3. An add-on system for an in vitro flow system, the add-on system providing means for controlling flow, pressure, and flow amplitude.

Clause 4. The add-on system of clause 3, wherein the in vitro flow system is a pulsatile or syringe flow system.

Clause 5. An improvement to an in vitro flow system that includes: a medical implant having an inner surface defining a bore, the bore having an inlet and an outlet; a fluid reservoir defining an inner chamber, the inner chamber configured to contain a desired fluid having at least one component, wherein the inner chamber of the fluid reservoir is in fluid communication with the outlet of the bore of the medical implant; a pump in fluid communication with the inner chamber of the fluid reservoir and the inlet of the bore of the medical implant, wherein the pump is configured to direct flow of the desired fluid to the inlet of the bore of the medical implant at a desired rate such that at least a portion of the inner surface of the medical implant contacts the desired fluid; and a first pressure valve positioned therebetween and in fluid communication with the outlet of the bore of the medical implant and the inner chamber of the fluid reservoir, wherein the first pressure valve is configured to modulate the flow of the desired fluid between the outlet of the bore of the medical implant and the inner chamber of the fluid reservoir, wherein the at least one component of the desired fluid includes at least one of nutrients, cells, proteins, and/or tissue; the improvement including at least one control element capable of changing local speed of fluid moving through the pressure valve.

Clause 6. An improvement to an in vitro flow system, the improvement including manipulating pressure in the system by increasing resistance on the outlet of the chamber using a variable valve.

Clause 7. The improvement of clause 6, wherein the system does not employ headspace gases to increase or decrease pressure in the system.

Clause 8. An improvement to an in vitro flow system, the improvement including manipulating a flow velocity of the fluid in order to mimic multiple different flow and pressure waveforms over a period of time.

Clause 9. An improvement to an in vitro flow system, the improvement including a single stage compliance chamber and no air pockets.

Clause 10. An improvement to the in vitro flow system of any one of clauses 1-9, the improvement including a 360-degree imaginable in situ chamber composed of a substantially transparent component base.

Clause 11. The improvement of clause 10, wherein the transparent component base includes vinyl, nylon, or silicone.

Clause 12. The improvement of any one of clauses 1, 2, or 5-11, wherein the in vitro flow system is a pulsatile flow system or syringe flow system.

Clause 13. The flow system or improved flow system of any of the prior clauses, including electronics and a 3D scaffold capable of running for more than seven days, at least two weeks, at least three weeks, at least four weeks, more than four weeks, at least a month, more than a month, or more than 2 months.

Clause 14. A high-throughput flow system, including the flow system or improved flow system of any of the prior clauses configured to run more than 12, more than 15, more than 18, more than 20, more than 22, or more than 24 chambers in parallel.

Clause 15. A flow limiting operator improvement to a fluid-management device or system, substantially as described herein.

Clause 16. A method of detecting and/or measuring a response of a biological cell or tissue to a change in fluid flow amplitude, the method including: contacting the biological cell or tissue with a fluid within flow system or improved flow system of any of clauses 1-14; changing the fluid flow amplitude of the fluid in contact with the biological cell or tissue; and observing and/or measuring a response of the biological cell or tissue during or after the change of fluid flow amplitude; optionally recording one or more characteristics of the response in a non-transitory computer readable medium.

Clause 17. A method of screening a test compound for effect(s) on a biological cell or tissue, the method including: contacting the biological cell or tissue with a fluid including the test compound within flow system or improved flow system of any of clauses 1-14; changing the fluid flow amplitude of the fluid in contact with the biological cell or tissue; and observing and/or measuring a response of the biological cell or tissue during or after the change of fluid flow amplitude; optionally recording one or more characteristics of the response in a non-transitory computer readable medium.

Clause 18. A system, including: a plurality of chambers, a respective chamber of the plurality of chambers having a respective primary end and a respective secondary end; a plurality of sensors, a respective sensor of the plurality of sensors being connected to the respective primary end or the secondary end of the respective chamber, the respective sensor being configured to sense a respective monitoring parameter associated with the respective chamber; a pump, connected to the respective primary end of the respective chamber, the pump being configured to move media to or from the respective chamber; a plurality of valves, a respective valve of the plurality of valves being connected to the respective secondary end or the primary end of the respective chamber, the respective valve being configured to control a fluid velocity of the media flowing through the respective chamber; and a flow limiting operator (FLO), electrically connected to the plurality of sensors, the pump, and the plurality of valves, the FLO being configured to independently control the respective chamber by manipulating one or more controllable parameters associated with the respective chamber based on the respective monitoring parameter associated with the respective chamber.

Clause 19. The system of clause 18, further including: a reservoir, connected between the pump and the respective valve, the reservoir being configured to contain the media.

Clause 20. The system of clause 18, further including: a plurality of additional sensors, a respective additional sensor of the plurality of additional sensors being connected to the respective secondary end or the primary end of the respective chamber, the respective additional sensor being configured to sense a respective additional parameter associated with the respective chamber.

Clause 21. The system of clause 20, wherein the FLO is further configured to be electrically connected to the plurality of additional sensors, the FLO being configured to receive the respective additional parameter associated with the respective chamber from the respective additional sensor.

Clause 22. The system of clause 18, further including: a plurality of to-be-tested components, a respective to-be-tested component of the plurality of to-be-tested components being connected between the pump and the respective valve of the plurality of valves, the respective to-be-tested component including biomaterial, and the respective to-be-tested component being configured to allow the media flowing through the chamber at least partially contact the biomaterial.

Clause 23. The system of clause 22, wherein the respective to-be-tested component is an implantable valve.

Clause 24. The system of clause 18, further including a user interface, configured to present information.

Clause 25. The system of clause 18, further including: a plurality of on/off switches, a respective on/off switch being configured to turn on/off the respective chamber.

Clause 26. The system of clause 18, further including: a plurality of actuators, a respective actuator being electrically connected between the FLO and the respective valve, the respective actuator being configured to drive the respective valve.

Clause 27. The system of clause 26, wherein the FLO is further configured to send a pump signal to the pump to set a status of the pump; receive the respective monitoring parameter associated with the respective chamber from the respective sensor; determine whether the respective monitoring parameter associated with the respective chamber is higher than a respective threshold; send a first driving signal to the respective actuator to drive the respective valve in a first direction upon determining that the respective monitoring parameter associated with the respective chamber is higher than the respective threshold; and/or send a second driving signal to the respective actuator to drive the respective valve in a second direction upon determining that the respective monitoring parameter associated with the respective chamber is lower than the respective threshold, the second direction being different from the first direction.

Clause 28. The system of clause 27, wherein the respective threshold is a function of time.

Clause 29. The system of clause 18, wherein the monitoring parameter includes at least one of a pressure of the media flowing through the respective chamber, a flow rate of the media flowing through the respective chamber, a waveform of the pressure of the media flowing through the respective chamber, and a waveform of the flow rate of the media flowing through the respective chamber.

Clause 30. The system of clause 18, wherein the respective monitoring parameter is a function of time.

Clause 31. The system of clause 18, wherein the one or more controllable parameters associated with the respective chamber include a pressure of the media flowing through the respective chamber, a flow rate of the media flowing through the respective chamber, an amplitude of a waveform of the flow rate of the media flowing through the respective chamber, a frequency of the waveform of the flow rate of the media flowing through the respective chamber, an amplitude of a waveform of the pressure of the media flowing through the respective chamber, a frequency of the waveform of the pressure of the media flowing through the respective chamber, and a resistance of the media flowing through the respective chamber.

Clause 32. The system of clause 14, wherein a unit of the flow rate of the media flowing through the respective chamber is ml/hr, a unit of the amplitude of the waveform of the flow rate of the media flowing through the respective chamber is Δflow rate/Δtime, a unit of the frequency of the waveform of the flow rate of the media flowing through the respective chamber is Hertz, a unit of an amplitude of the waveform of the pressure of the media flowing through the respective chamber is mmHg, a unit of the frequency of the waveform of the pressure of the media flowing through the respective chamber is Hertz, and a unit of the resistance of the media flowing through the respective chamber is mmHg*hr*ml^-1.

Clause 33. The system of clause 18, wherein the FLO is further configured to communicate with a network.

Clause 34. The system of clause 18, wherein the respective chamber is detachable from the system.

Clause 35. The system of clause 18, wherein the respective chamber is a compliance chamber.

Clause 36. The system of clause 18, wherein the respective chamber is configured to allow the media containing biomaterial to flow through.

Clause 37. A method, including: sending a pump signal to a pump to set a status of the pump, the pump being connected to a respective primary end of a respective chamber of a plurality of chambers, the pump being configured to move media to or from the respective chamber; receiving a respective monitoring parameter associated with the respective chamber from a respective sensor of a plurality of sensors, the respective sensor being connected to a respective primary end or a secondary end of the respective chamber, and the respective sensor being configured to sense the respective monitoring parameter associated with the respective chamber; and independently controlling the respective chamber by manipulating one or more controllable parameters associated with the respective chamber based on the respective monitoring parameter associated with the respective chamber.

Clause 38. The method of clause 37, wherein independently controlling the respective chamber includes: determining whether the respective monitoring parameter associated with the respective chamber is higher than a respective threshold; sending a first driving signal to a respective actuator of a plurality of actuators to drive a respective valve of a plurality of valves in a first direction upon determining that the respective monitoring parameter associated with the respective chamber is higher than the respective threshold, the respective valve being connected to the respective secondary end or the primary end of the respective chamber, the respective valve being configured to control a fluid velocity of the media flowing through the respective chamber; and/or sending a second driving signal to the respective actuator to drive the respective valve in a second direction upon determining that the respective monitoring parameter associated with the respective chamber is lower than the respective threshold, the second direction being different from the first direction.

Clause 39. The method of clause 38, wherein the respective monitoring parameter is a function of time, and the respective threshold is a function of time.

Clause 40. The method of clause 37, further including: receiving a respective additional parameter from a respective additional sensor of a plurality of additional sensors, the respective additional sensor being connected to the respective secondary end or the primary end of the respective chamber, the respective additional sensor being configured to sense the respective additional parameter associated with the respective chamber.

Clause 41. The method of clause 37, further including: storing data associated with the respective chamber in a storage component.

Clause 42. The method of clause 37, further including: presenting information on a user interface.

Clause 43. The method of clause 37, further including: receiving a respective input via a respective on/off switch of a plurality of on/off switches; and turning on/off the respective chamber based on the respective input.

Clause 44. A computer-readable medium storing computer-readable instructions executable by one or more processors, that when executed by the one or more processors, causes the one or more processors to perform acts including: sending a pump signal to a pump to set a status of the pump, the pump being connected to a respective primary end of a respective chamber of a plurality of chambers, the pump being configured to move media to or from the respective chamber; receiving a respective monitoring parameter associated with the respective chamber from a respective sensor of a plurality of sensors, the respective sensor being connected to a respective primary end or a secondary end of the respective chamber, and the respective sensor being configured to sense the respective monitoring parameter associated with the respective chamber; and independently controlling the respective chamber by manipulating one or more controllable parameters associated with the respective chamber based on the respective monitoring parameter associated with the respective chamber.

Clause 45. The computer-readable medium of clause 44, wherein independently controlling the one or more controllable parameters associated with the respective chamber includes: determining whether the respective monitoring parameter associated with the respective chamber is higher than a respective threshold; sending a first driving signal to a respective actuator of a plurality of actuators to drive a respective valve of a plurality of valves in a first direction upon determining that the respective monitoring parameter associated with the respective chamber is higher than the respective threshold, the respective valve being connected to the respective secondary end or the primary end of the respective chamber, the respective valve being configured to control a fluid velocity of the media flowing through the respective chamber; and/or sending a second driving signal to the respective actuator to drive the respective valve in a second direction upon determining that the respective monitoring parameter associated with the respective chamber is lower than the respective threshold, the second direction being different to the first direction.

Clause 46. The computer-readable medium of clause 45, wherein the respective monitoring parameter is a function of time, and the respective threshold is a function of time.

Clause 47. An apparatus, including: one or more processors, and memory, coupled to the one or more processors, the memory storing thereon computer-executable modules, executable by the one or more processors, the computer-executable modules including: a pump control module, configured to send a pump signal to a pump to set a status of the pump, the pump being connected to a respective primary end of a respective chamber of a plurality of chambers, the pump being configured to move media to or from the respective chamber; a monitoring parameter receiving module, configured to receive a respective monitoring parameter associated with the respective chamber from a respective sensor of a plurality of sensors, the respective sensor being connected to a respective primary end or a secondary end of the respective chamber, and the respective sensor being configured to sense the respective monitoring parameter associated with the respective chamber; and a control module, configured to independently control the respective chamber by manipulating one or more controllable parameters associated with the respective chamber based on the respective monitoring parameter associated with the respective chamber.

Clause 48. The apparatus of clause 47, wherein the control module is further configured to: determine whether the respective monitoring parameter associated with the respective chamber is higher than a respective threshold; send a first driving signal to a respective actuator of a plurality of actuators to drive a respective valve of a plurality of valves in a first direction upon determining that the respective monitoring parameter associated with the respective chamber is higher than the respective threshold, the respective valve being connected to the respective secondary end or the primary end of the respective chamber, the respective valve being configured to control a fluid velocity of the media flowing through the respective chamber; and/or send a second driving signal to the respective actuator to drive the respective valve in a second direction upon determining that the respective monitoring parameter associated with the respective chamber is lower than the respective threshold, the second direction being different from the first direction.

Clause 49. The apparatus of clause 48 wherein the respective monitoring parameter is a function of time, and the respective threshold is a function of time.

What is claimed is:

1. A system, comprising:

a plurality of chambers, a respective chamber of the plurality of chambers having a respective primary end and a respective secondary end;

a plurality of sensors, a respective sensor of the plurality of sensors being connected to the respective primary end or the secondary end of the respective chamber, the respective sensor being configured to sense a respective monitoring parameter associated with the respective chamber;

a pump, connected to the respective primary end or secondary end of the respective chamber, the pump being configured to move media to or from the respective chamber;

a plurality of valves, a respective valve of the plurality of valves being connected to the respective secondary end or the primary end of the respective chamber, the respective valve being configured to control a fluid velocity of the media flowing through the respective chamber; and a flow limiting operator (FLO), electrically connected to the plurality of sensors, the pump, and the plurality of valves, the FLO being configured to independently control the respective chamber by manipulating one or more controllable parameters associated with the respective chamber based on the respective monitoring parameter associated with the respective chamber;

wherein the one or more controllable parameters associated with the respective chamber include a pressure of the media flowing through the respective chamber, a flow rate of the media flowing through the respective chamber, an amplitude of a waveform of the flow rate of the media flowing through the respective chamber, a frequency of the waveform of the flow rate of the media flowing through the respective chamber, an amplitude of a waveform of the pressure of the media flowing through the respective chamber, a frequency of the waveform of the pressure of the media flowing through the respective chamber, and a resistance of the media flowing through the respective chamber.

2. The system of claim 1, further comprising:

a reservoir, connected between the pump and the respective valve, the reservoir being configured to contain the media.

3. The system of claim 1, further comprising:

a plurality of additional sensors, a respective additional sensor of the plurality of additional sensors being connected to the respective secondary end or the primary end of the respective chamber, the respective additional sensor being configured to sense a respective additional parameter associated with the respective chamber.

4. The system of claim 3, wherein the FLO is further configured to be electrically connected to the plurality of additional sensors, the FLO being configured to receive the respective additional parameter associated with the respective chamber from the respective additional sensor.

5. The system of claim 1, further comprising:

a plurality of to-be-tested components, a respective to-be-tested component of the plurality of to-be-tested components being connected between the pump and the respective valve of the plurality of valves, the respective to-be-tested component including biomaterial, and the respective to-be-tested component being configured to allow the media flowing through the chamber at least partially contact the biomaterial.

6. The system of claim 5, wherein the respective to-be-tested component is an implantable valve.

7. The system of claim 1, further comprising a user interface, configured to present information.

8. The system of claim 1, further comprising:

a plurality of on/off switches, a respective on/off switch being configured to turn on/off the respective chamber.

9. The system of claim 1, further comprising:

a plurality of actuators, a respective actuator being electrically connected between the FLO and the respective valve, the respective actuator being configured to drive the respective valve.

10. The system of claim 9, wherein the FLO is further configured to send a pump signal to the pump to set a status of the pump;

receive the respective monitoring parameter associated with the respective chamber from the respective sensor;

determine whether the respective monitoring parameter associated with the respective chamber is higher than a respective threshold;

send a first driving signal to the respective actuator to drive the respective valve in a first direction upon determining that the respective monitoring parameter associated with the respective chamber is higher than the respective threshold; and/or send a second driving signal to the respective actuator to drive the respective valve in a second direction upon determining that the respective monitoring parameter associated with the respective chamber is lower than the respective threshold, the second direction being different from the first direction.

11. The system of claim 10, wherein the respective threshold is a function of time.

12. The system of claim 1, wherein the monitoring parameter includes at least one of a pressure of the media flowing through the respective chamber, a flow rate of the media flowing through the respective chamber, a waveform of the pressure of the media flowing through the respective chamber, and/or a waveform of the flow rate of the media flowing through the respective chamber.

13. The system of claim 1, wherein the respective monitoring parameter is a function of time.

14. The system of claim 1, wherein a unit of the flow rate of the media flowing through the respective chamber is ml/hr, a unit of the amplitude of the waveform of the flow rate of the media flowing through the respective chamber is Δflow rate/Δtime, a unit of the frequency of the waveform of the flow rate of the media flowing through the respective chamber is Hertz, a unit of an amplitude of the waveform of the pressure of the media flowing through the respective chamber is mmHg, a unit of the frequency of the waveform of the pressure of the media flowing through the respective chamber is Hertz, and a unit of the resistance of the media flowing through the respective chamber is mmHg*hr*ml^-1.

15. The system of claim 1, wherein the FLO is further configured to communicate with a network.

16. A system, comprising:

a plurality of chambers, a respective chamber of the plurality of chambers having a respective primary end and a respective secondary end;

a plurality of sensors, a respective sensor of the plurality of sensors being connected to the respective primary end or the secondary end of the respective chamber, the respective sensor being configured to sense a respective monitoring parameter associated with the respective chamber;

a pump, connected to the respective primary or secondary end of the respective chamber, the pump being configured to move media to or from the respective chamber;

a plurality of valves, a respective valve of the plurality of valves being connected to the respective secondary end or the primary end of the respective chamber, the respective valve being configured to control a fluid velocity of the media flowing through the respective chamber; and a flow limiting operator (FLO), electrically connected to the plurality of sensors, the pump, and the plurality of valves, the FLO being configured to independently control the respective chamber by manipulating one or more controllable parameters associated with the respective chamber based on the respective monitoring parameter associated with the respective chamber, wherein the respective chamber is detachable from the system.

17. A system, comprising:

a plurality of chambers, a respective chamber of the plurality of chambers having a respective primary end and a respective secondary end;

a plurality of sensors, a respective sensor of the plurality of sensors being connected to the respective primary end or the secondary end of the respective chamber, the respective sensor being configured to sense a respective monitoring parameter associated with the respective chamber;

a pump, connected to the respective primary or secondary end of the respective chamber, the pump being configured to move media to or from the respective chamber;

a plurality of valves, a respective valve of the plurality of valves being connected to the respective secondary end or the primary end of the respective chamber, the respective valve being configured to control a fluid velocity of the media flowing through the respective chamber; and a flow limiting operator (FLO), electrically connected to the plurality of sensors, the pump, and the plurality of valves, the FLO being configured to independently control the respective chamber by manipulating one or more controllable parameters associated with the respective chamber based on the respective monitoring parameter associated with the respective chamber, wherein the respective chamber is a compliance chamber.

18. The system of claim 1, wherein the respective chamber is configured to allow the media containing biomaterial to flow through.

* * * * *